United States Patent
Halkier et al.

(10) Patent No.: US 6,649,814 B2
(45) Date of Patent: Nov. 18, 2003

(54) CYTOCHROME P450 MONOOXYGENASES

(75) Inventors: Barbara Ann Halkier, Copenhagen (DK); Sören Bak, Copenhagen (DK); Rachel Alice Kahn, Copenhagen (DK); Birger Lindberg Möller, Bronshoj (DK)

(73) Assignees: Syngenta Participations AG, Basel (CH); Royal Veterinary and Agricultural University, Copenhagen (DK)

( * ) Notice: Subject to any disclaimer, the term of this patent is extended or adjusted under 35 U.S.C. 154(b) by 216 days.

(21) Appl. No.: 09/899,642

(22) Filed: Jul. 5, 2001

(65) Prior Publication Data

US 2003/0041346 A1 Feb. 27, 2003

Related U.S. Application Data

(62) Division of application No. 09/380,420, filed as application No. PCT/EP98/01253 on Mar. 5, 1998, now Pat. No. 6,300,544.

(30) Foreign Application Priority Data

Mar. 7, 1997 (DE) .......................... 978 10 132
Dec. 8, 1997 (DE) .......................... 978 10 954

(51) Int. Cl.$^7$ .......................... A01H 1/00; C07H 21/04; C07K 14/415; C12N 5/14; C12N 9/00
(52) U.S. Cl. .................. 800/302; 435/183; 435/418; 435/419; 435/320.1; 530/350; 530/370; 536/23.2; 536/23.6; 800/278; 800/279; 800/295; 800/301
(58) Field of Search ................. 435/183, 418, 435/419, 320.1; 530/350, 370; 536/23.2, 23.6; 800/278, 279, 295, 301, 302

(56) References Cited

U.S. PATENT DOCUMENTS 5,882,851 A   3/1999   Koch et al.

FOREIGN PATENT DOCUMENTS

WO    WO 93/22441    11/1993
WO    WO 95/16041    6/1995

OTHER PUBLICATIONS

Koch et al., Archives of Biochemistry and Biophysics, 292(1): 141–150 (1992).
Kahn et al., Plant Physiology, 115(4): 1661–1670 (1997).
Maughan et al., GenBank Accession No. T52254, submitted May 1996.

Primary Examiner—Phuong T. Bui
(74) Attorney, Agent, or Firm—Gregory W. Warren

(57) ABSTRACT

Cytochrome P450$_{II}$ dependent monooxygenases and DNA molecules encoding these monooxygenases are provided, which are able to catalyze the biosynthethic conversion of aldoximes to nitrils and the conversion of said nitrils to the corresponding cyanohydrins, which are the presursors of cyanogenic glycosides. Moreover, the invention provides methods for obtaining DNA molecules according to the invention and methods for obtaining transgenic plants resistant to insects, acarids, or nematodes or plants with improved nutritive value.

9 Claims, No Drawings

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 1929 base pairs
      (B) TYPE: nucleic acid
      (C) STRANDEDNESS: double
      (D) TOPOLOGY: linear (ii) MOLECULE TYPE: cDNA (vii) IMMEDIATE SOURCE:
      (B) CLONE: P450ox (ix) FEATURE:
      (A) NAME/KEY: CDS
      (B) LOCATION: 81..1673

(xi) SEQUENCE DESCRIPTION: SEQ ID NO: 1:

```
CAGAGCTAGA AGCAGCTCAC ACTCCACACT CGTCTCGCCC GGCCATACCC CAAGGCAAGC        60

AGGGGCACGG GCAATTAACA ATG GCC ACC ACC GCC ACC CCG CAG CTC CTC          110
                      Met Ala Thr Thr Ala Thr Pro Gln Leu Leu
                       1               5                   10

GGC GGC AGC GTG CCG CAG CAG TGG CAG ACG TGC CTC CTG GTG CTC CTC        158
Gly Gly Ser Val Pro Gln Gln Trp Gln Thr Cys Leu Leu Val Leu Leu
                 15                  20                  25

CCT GTG CTG CTG GTG TCC TAC TAC CTC CTC ACC AGC AGG AGC AGG AAC        206
Pro Val Leu Leu Val Ser Tyr Tyr Leu Leu Thr Ser Arg Ser Arg Asn
             30                  35                  40
```

-continued

| | |
|---|---|
| AGG AGC AGG AGC GGC AAG CTG GGC GGG GCG CCG CGG CTG CCG CCG GGC<br>Arg Ser Arg Ser Gly Lys Leu Gly Gly Ala Pro Arg Leu Pro Pro Gly<br>           45                      50                     55 | 254 |
| CCT GCG CAG CTG CCG ATC CTG GGC AAC CTG CAC CTG CTG GGC CCG CTG<br>Pro Ala Gln Leu Pro Ile Leu Gly Asn Leu His Leu Leu Gly Pro Leu<br>           60                      65                     70 | 302 |
| CCG CAC AAG AAC CTC CGC GAG CTG GCG CGG CGG TAC GGC CCC GTG ATG<br>Pro His Lys Asn Leu Arg Glu Leu Ala Arg Arg Tyr Gly Pro Val Met<br>75                      80                     85                   90 | 350 |
| CAG CTC CGT CTA GGC ACC GTG CCG ACG GTG GTG GTG TCC AGC GCG GAG<br>Gln Leu Arg Leu Gly Thr Val Pro Thr Val Val Val Ser Ser Ala Glu<br>                     95                    100                  105 | 398 |
| GCG GCG CGG GAG GTT CTC AAG GTG CAC GAC GTC GAC TGC TGC AGC CGG<br>Ala Ala Arg Glu Val Leu Lys Val His Asp Val Asp Cys Cys Ser Arg<br>               110                    115                  120 | 446 |
| CCG GCG TCG CCC GGT CCC AAG CGC CTC TCC TAC GAC CTC AAG AAC GTC<br>Pro Ala Ser Pro Gly Pro Lys Arg Leu Ser Tyr Asp Leu Lys Asn Val<br>             125                    130                  135 | 494 |
| GGC TTC GCG CCC TAC GGC GAG TAC TGG CGC GAG ATG CGC AAG CTC TTC<br>Gly Phe Ala Pro Tyr Gly Glu Tyr Trp Arg Glu Met Arg Lys Leu Phe<br>      140                    145                  150 | 542 |
| GCG CTC GAG CTC CTC AGC ATG CGC CGT GTC AAG GCC GCC TGC TAC GCG<br>Ala Leu Glu Leu Leu Ser Met Arg Arg Val Lys Ala Ala Cys Tyr Ala<br>155                    160                  165                170 | 590 |
| CGC GAG CAG GAG ATG GAC AGG CTC GTC GCC GAC CTC GAC CGC GCC GCC<br>Arg Glu Gln Glu Met Asp Arg Leu Val Ala Asp Leu Asp Arg Ala Ala<br>             175                    180                  185 | 638 |
| GCG TCC AAG GCC TCC ATC GTC CTC AAC GAC CAC GTC TTC GCC CTC ACC<br>Ala Ser Lys Ala Ser Ile Val Leu Asn Asp His Val Phe Ala Leu Thr<br>             190                    195                  200 | 686 |
| GAC GGC ATC ATC GGC ACC GTC GCG TTC GGC AAC ATC TAC GCC TCC AAG<br>Asp Gly Ile Ile Gly Thr Val Ala Phe Gly Asn Ile Tyr Ala Ser Lys<br>      205                    210                  215 | 734 |
| CAG TTC GCG CAC AAG GAG CGC TTC CAG CAC GTG CTG GAC GAC GCC ATG<br>Gln Phe Ala His Lys Glu Arg Phe Gln His Val Leu Asp Asp Ala Met<br>220                    225                  230 | 782 |
| GAC ATG ATG GCC AGC TTC TCC GCC GAG GAC TTC TTC CCC AAC GCC GCC<br>Asp Met Met Ala Ser Phe Ser Ala Glu Asp Phe Phe Pro Asn Ala Ala<br>235                    240                  245              250 | 830 |
| GGC CGC CTC GCC GAC CGC CTC TCG GGC TTC CTC GCC CGC CGC GAG CGC<br>Gly Arg Leu Ala Asp Arg Leu Ser Gly Phe Leu Ala Arg Arg Glu Arg<br>             255                    260                  265 | 878 |
| ATC TTC AAC GAG CTC GAC GTC TTC TTC GAG AAG GTC ATC GAC CAG CAC<br>Ile Phe Asn Glu Leu Asp Val Phe Phe Glu Lys Val Ile Asp Gln His<br>             270                    275                  280 | 926 |
| ATG GAC CCG GCG CGC CCC GTC CCG GAC AAC GGC GGC GAC CTC GTC GAC<br>Met Asp Pro Ala Arg Pro Val Pro Asp Asn Gly Gly Asp Leu Val Asp<br>             285                    290                  295 | 974 |
| GTC CTC ATC AAC CTG TGC AAG GAG CAC GAC GGC ACG CTC CGC TTC ACC<br>Val Leu Ile Asn Leu Cys Lys Glu His Asp Gly Thr Leu Arg Phe Thr<br>300                    305                  310 | 1022 |
| AGG GAC CAC GTC AAG GCC ATC GTC CTC GAC ACC TTC ATC GGC GCC ATC<br>Arg Asp His Val Lys Ala Ile Val Leu Asp Thr Phe Ile Gly Ala Ile<br>315                    320                  325              330 | 1070 |
| GAC ACC AGC TCC GTC ACC ATC CTG TGG GCC ATG TCG GAG CTG ATG CGG<br>Asp Thr Ser Ser Val Thr Ile Leu Trp Ala Met Ser Glu Leu Met Arg<br>             335                    340                  345 | 1118 |
| AAG CCG CAG GTG CTG AGG AAG GCG CAG GCC GAG GTG CGG GCC GCC GTG<br>Lys Pro Gln Val Leu Arg Lys Ala Gln Ala Glu Val Arg Ala Ala Val<br>             350                    355                  360 | 1166 |

-continued

```
GGC GAC GAC AAG CCG CGC GTC AAC TCG GAA GAC GCC GCC AAG ATC CCG    1214
Gly Asp Asp Lys Pro Arg Val Asn Ser Glu Asp Ala Ala Lys Ile Pro
            365                 370                 375

TAC CTG AAG ATG GTG GTC AAG GAG ACG CTG CGG CTG CAC CCG CCG GCG    1262
Tyr Leu Lys Met Val Val Lys Glu Thr Leu Arg Leu His Pro Pro Ala
    380                 385                 390

ACG CTG CTG GTG CCC CGG GAG ACG ATG CGG GAC ACC ACC ATC TGC GGC    1310
Thr Leu Leu Val Pro Arg Glu Thr Met Arg Asp Thr Thr Ile Cys Gly
395                 400                 405                 410

TAC GAC GTG CCG GCC AAC ACG CGC GTC TTC GTC AAC GCC TGG GCC ATC    1358
Tyr Asp Val Pro Ala Asn Thr Arg Val Phe Val Asn Ala Trp Ala Ile
                415                 420                 425

GGC AGG GAC CCG GCG AGC TGG CCG GCG CCC GAC GAG TTC AAC CCG GAC    1406
Gly Arg Asp Pro Ala Ser Trp Pro Ala Pro Asp Glu Phe Asn Pro Asp
            430                 435                 440

CGC TTC GTG GGG AGC GAC GTC GAC TAC TAC GGC TCG CAC TTC GAG CTC    1454
Arg Phe Val Gly Ser Asp Val Asp Tyr Tyr Gly Ser His Phe Glu Leu
    445                 450                 455

ATA CCG TTC GGG GCC GGC CGC CGG ATC TGC CCG GGA CTC ACC ATG GGC    1502
Ile Pro Phe Gly Ala Gly Arg Arg Ile Cys Pro Gly Leu Thr Met Gly
460                 465                 470

GAG ACC AAC GTC ACC TTC ACC CTC GCC AAC CTG CTC TAC TGC TAC GAC    1550
Glu Thr Asn Val Thr Phe Thr Leu Ala Asn Leu Leu Tyr Cys Tyr Asp
475                 480                 485                 490

TGG GCG CTG CCG GGG GCC ATG AAG CCG GAG GAC GTC AGC ATG GAG GAG    1598
Trp Ala Leu Pro Gly Ala Met Lys Pro Glu Asp Val Ser Met Glu Glu
                495                 500                 505

ACC GGA GCG CTC ACG TTC CAC CGG AAG ACG CCG CTT GTG GTG GTG CCC    1646
Thr Gly Ala Leu Thr Phe His Arg Lys Thr Pro Leu Val Val Val Pro
            510                 515                 520

ACC AAA TAC AAG AAC CGC CGC GCC GCC TAGTGAGCAG AGCCGAGCAG          1693
Thr Lys Tyr Lys Asn Arg Arg Ala Ala
    525                 530

AGCAATGGTC GACGACGACG ACGACGACGA CTGAATAAGC GTGCCAAAGT TTAGTACT    1753

GTACGTACGT ACCTACTGCT ACTACGTACA GCTAGCCAAC AGTCAGAGTT GGACACTG    1813

GGAGCTATCA TCCGGTCCTC TTCTTTTTGT GATACGTATT TGTTATGTGT TTTAGTGC    1873

CAAAGCACAA AAGAAATAAA GCCCATCACA GTCGCGAGTC AAAAAAAAAA AAAAAA      1929

(2) INFORMATION FOR SEQ ID NO: 2:

(i) SEQUENCE CHARACTERISTICS:
        (A) LENGTH: 531 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Thr Thr Ala Thr Pro Gln Leu Leu Gly Gly Ser Val Pro Gln
 1               5                  10                  15

Gln Trp Gln Thr Cys Leu Leu Val Leu Leu Pro Val Leu Leu Val Ser
                20                  25                  30

Tyr Tyr Leu Leu Thr Ser Arg Ser Arg Asn Arg Ser Arg Ser Gly Lys
            35                  40                  45

Leu Gly Gly Ala Pro Arg Leu Pro Gly Pro Ala Gln Leu Pro Ile
        50                  55                  60

Leu Gly Asn Leu His Leu Leu Gly Pro Leu Pro His Lys Asn Leu Arg
65                  70                  75                  80
```

-continued

Glu Leu Ala Arg Arg Tyr Gly Pro Val Met Gln Leu Arg Leu Gly Thr
                85                  90                  95
Val Pro Thr Val Val Ser Ser Ala Glu Ala Arg Glu Val Leu
            100                 105                 110
Lys Val His Asp Val Asp Cys Cys Ser Arg Pro Ala Ser Pro Gly Pro
            115                 120                 125
Lys Arg Leu Ser Tyr Asp Leu Lys Asn Val Gly Phe Ala Pro Tyr Gly
            130                 135                 140
Glu Tyr Trp Arg Glu Met Arg Lys Leu Phe Ala Leu Glu Leu Leu Ser
145                 150                 155                 160
Met Arg Arg Val Lys Ala Ala Cys Tyr Ala Arg Glu Gln Glu Met Asp
                165                 170                 175
Arg Leu Val Ala Asp Leu Asp Arg Ala Ala Ala Ser Lys Ala Ser Ile
                180                 185                 190
Val Leu Asn Asp His Val Phe Ala Leu Thr Asp Gly Ile Ile Gly Thr
                195                 200                 205
Val Ala Phe Gly Asn Ile Tyr Ala Ser Lys Gln Phe Ala His Lys Glu
                210                 215                 220
Arg Phe Gln His Val Leu Asp Asp Ala Met Asp Met Met Ala Ser Phe
225                 230                 235                 240
Ser Ala Glu Asp Phe Phe Pro Asn Ala Ala Gly Arg Leu Ala Asp Arg
                245                 250                 255
Leu Ser Gly Phe Leu Ala Arg Arg Glu Arg Ile Phe Asn Glu Leu Asp
                260                 265                 270
Val Phe Phe Glu Lys Val Ile Asp Gln His Met Asp Pro Ala Arg Pro
                275                 280                 285
Val Pro Asp Asn Gly Gly Asp Leu Val Asp Val Leu Ile Asn Leu Cys
                290                 295                 300
Lys Glu His Asp Gly Thr Leu Arg Phe Thr Arg Asp His Val Lys Ala
305                 310                 315                 320
Ile Val Leu Asp Thr Phe Ile Gly Ala Ile Asp Thr Ser Ser Val Thr
                325                 330                 335
Ile Leu Trp Ala Met Ser Glu Leu Met Arg Lys Pro Gln Val Leu Arg
                340                 345                 350
Lys Ala Gln Ala Glu Val Arg Ala Ala Val Gly Asp Asp Lys Pro Arg
                355                 360                 365
Val Asn Ser Glu Asp Ala Ala Lys Ile Pro Tyr Leu Lys Met Val Val
                370                 375                 380
Lys Glu Thr Leu Arg Leu His Pro Pro Ala Thr Leu Leu Val Pro Arg
385                 390                 395                 400
Glu Thr Met Arg Asp Thr Thr Ile Cys Gly Tyr Asp Val Pro Ala Asn
                405                 410                 415
Thr Arg Val Phe Val Asn Ala Trp Ala Ile Gly Arg Asp Pro Ala Ser
                420                 425                 430
Trp Pro Ala Pro Asp Glu Phe Asn Pro Asp Arg Phe Val Gly Ser Asp
                435                 440                 445
Val Asp Tyr Tyr Gly Ser His Phe Glu Leu Ile Pro Phe Gly Ala Gly
                450                 455                 460
Arg Arg Ile Cys Pro Gly Leu Thr Met Gly Glu Thr Asn Val Thr Phe
465                 470                 475                 480
Thr Leu Ala Asn Leu Leu Tyr Cys Tyr Asp Trp Ala Leu Pro Gly Ala
                485                 490                 495

```
Met Lys Pro Glu Asp Val Ser Met Glu Glu Thr Gly Ala Leu Thr Phe
            500                 505                 510

His Arg Lys Thr Pro Leu Val Val Val Pro Thr Lys Tyr Lys Asn Arg
            515                 520                 525

Arg Ala Ala
    530
```

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: unknown
        (D) TOPOLOGY: linear (ii) MOLECULE TYPE: peptide (v) FRAGMENT TYPE: N-terminal (vii) IMMEDIATE SOURCE:
        (B) CLONE: N-terminal peptide (xi) SEQUENCE DESCRIPTION: SEQ ID NO: 3:

```
Ala Thr Thr Ala Thr Pro Gln Leu Leu Gly Gly Ser Val Pro Glu Gln
1               5                   10                  15
```

(2) INFORMATION FOR SEQ ID NO: 4:

(i) SEQUENCE CHARACTERISTICS:
        (A) LENGTH: 13 amino acids
        (B) TYPE: amino acid
        (C) STRANDEDNESS: unknown
        (D) TOPOLOGY: linear (ii) MOLECULE TYPE: peptide (v) FRAGMENT TYPE: internal (vii) IMMEDIATE SOURCE:
        (B) CLONE: Internal peptide (xi) SEQUENCE DESCRIPTION: SEQ ID NO: 4:

```
Met Asp Arg Leu Val Ala Asp Leu Asp Arg Ala Ala Ala
1               5                   10
```

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Primer 1

(ix) FEATURE:
        (A) NAME/KEY: misc_feature
        (B) LOCATION: 13..15
        (D) OTHER INFORMATION: /note= "N = inosine"

(xi) SEQUENCE DESCRIPTION: SEQ ID NO: 5:

GCGGAATTCT TYNNNCCNGA RMGNTT                                      26

(2) INFORMATION FOR SEQ ID NO: 6:

(i) SEQUENCE CHARACTERISTICS:
        (A) LENGTH: 6 amino acids

```
        (B) TYPE: amino acid
        (C) STRANDEDNESS: unknown
        (D) TOPOLOGY: linear (ii) MOLECULE TYPE: peptide (v) FRAGMENT TYPE: internal (vii) IMMEDIATE SOURCE:
        (B) CLONE: Amino acids encoded by primer 1

(xi) SEQUENCE DESCRIPTION: SEQ ID NO: 6:

Phe Xaa Pro Glu Arg Phe
1               5

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Primer 2

(ix) FEATURE:
        (A) NAME/KEY: misc_feature
        (B) LOCATION: 9..11
        (D) OTHER INFORMATION: /note= "N = inosine"

(ix) FEATURE:
        (A) NAME/KEY: misc_feature
        (B) LOCATION: 15..17
        (D) OTHER INFORMATION: /note= "N = inosine"

(xi) SEQUENCE DESCRIPTION: SEQ ID NO: 7:

GCGGATCCNN NRCANNNNCK NCKNCC                                              26

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: unknown
        (D) TOPOLOGY: linear (ii) MOLECULE TYPE: peptide (v) FRAGMENT TYPE: internal (vii) IMMEDIATE SOURCE:
        (B) CLONE: Amino acids encoded by primer 2

(xi) SEQUENCE DESCRIPTION: SEQ ID NO: 8:

Gly Arg Arg Xaa Cys Xaa Gly
1               5

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: T7 primer
```

```
        (xi) SEQUENCE DESCRIPTION: SEQ ID NO: 9:

AATACGACTC ACTATAG                                                      17

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: "12" gene specific primer (xi) SEQUENCE DESCRIPTION: SEQ ID NO: 10:

GCGGATCCGA CTACTACGGC TCGC                                              24

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GCGGATCCTT TTTTTTTTTT TTTTV                                             25

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: "7" gene specific primer (xi) SEQUENCE DESCRIPTION: SEQ ID NO: 12:

GCGGATCCGA CATCAAGGGC AGCG                                              24

(2) INFORMATION FOR SEQ ID NO: 13:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Primer 3

(xi) SEQUENCE DESCRIPTION: SEQ ID NO: 13:

CGCGGATCCA TATGGACGCA TCATTACTCC TCTCCGTCGC GCTC                        44

(2) INFORMATION FOR SEQ ID NO: 14:

(i) SEQUENCE CHARACTERISTICS:
        (A) LENGTH: 31 base pairs
        (B) TYPE: nucleic acid
```

(C) STRANDEDNESS: single
            (D) TOPOLOGY: linear (ii) MOLECULE TYPE: DNA (genomic)

(vii) IMMEDIATE SOURCE:
            (B) CLONE: Primer 4

(xi) SEQUENCE DESCRIPTION: SEQ ID NO: 14:

CGCAAGCTTA TTACATCTCA ACGGGGACCC T                                31

(2) INFORMATION FOR SEQ ID NO: 15:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: Primer 5

(xi) SEQUENCE DESCRIPTION: SEQ ID NO: 15:

CGCGGATCCA TATGGCAACA ACAGCAACCC CGCAGCTCCT C                     41

(2) INFORMATION FOR SEQ ID NO: 16:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: Primer 6

(xi) SEQUENCE DESCRIPTION: SEQ ID NO: 16:

CGCAAGCTTA TTATGCTGCG CGGCGGTTCT TGTATTTGG                        39

(2) INFORMATION FOR SEQ ID NO: 17:

(i) SEQUENCE CHARACTERISTICS:
            (A) LENGTH: 542 amino acids
            (B) TYPE: amino acid
            (C) STRANDEDNESS: unknown
            (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
            (B) STRAIN: Sinapis alba (xi) SEQUENCE DESCRIPTION: SEQ ID NO: 17:

Met Asn Thr Phe Thr Ser Asn Ser Ser Asp Leu Thr Ser Thr Thr Lys
1               5                   10                  15

Gln Thr Leu Ser Phe Ser Asn Met Tyr Leu Leu Thr Thr Leu Gln Ala
                20                  25                  30

Phe Val Ala Ile Thr Leu Val Met Leu Leu Lys Lys Val Leu Val Asn
            35                  40                  45

```
Asp Thr Asn Lys Lys Leu Ser Leu Pro Pro Gly Pro Thr Gly Trp
     50                  55                  60

Pro Ile Ile Gly Met Val Pro Thr Met Leu Lys Ser Arg Pro Val Phe
 65                  70                  75                  80

Arg Trp Leu His Ser Ile Met Lys Gln Leu Asn Thr Glu Ile Ala Cys
                 85                  90                  95

Val Arg Leu Gly Ser Thr His Val Ile Thr Val Thr Cys Pro Lys Ile
                100                 105                 110

Ala Arg Glu Val Leu Lys Gln Gln Asp Ala Leu Phe Ala Ser Arg Pro
            115                 120                 125

Met Thr Tyr Ala Gln Asn Val Leu Ser Asn Gly Tyr Lys Thr Cys Val
    130                 135                 140

Ile Thr Pro Phe Gly Glu Gln Phe Lys Lys Met Arg Lys Val Val Met
145                 150                 155                 160

Thr Glu Leu Val Cys Pro Ala Arg His Arg Trp Leu His Gln Lys Arg
                165                 170                 175

Ala Glu Glu Asn Asp His Leu Thr Ala Trp Val Tyr Asn Met Val Asn
            180                 185                 190

Asn Ser Asp Ser Val Asp Phe Arg Phe Val Thr Arg His Tyr Cys Gly
        195                 200                 205

Asn Ala Ile Lys Lys Leu Met Phe Gly Thr Arg Thr Phe Ser Gln Asn
    210                 215                 220

Thr Ala Pro Asn Gly Gly Pro Thr Ala Glu Asp Ile Glu His Met Gly
225                 230                 235                 240

Ala Met Phe Glu Ala Leu Gly Phe Thr Phe Ser Phe Cys Ile Ser Asp
                245                 250                 255

Tyr Leu Pro Ile Leu Thr Gly Leu Asp Leu Asn Gly His Glu Lys Ile
                260                 265                 270

Met Arg Asp Ser Ser Ala Ile Met Asp Lys Tyr His Asp Pro Ile Ile
            275                 280                 285

Asp Ala Arg Ile Lys Met Trp Arg Glu Gly Lys Lys Thr Gln Ile Glu
    290                 295                 300

Asp Phe Leu Asp Ile Phe Ile Ser Ile Lys Asp Glu Glu Gly Asn Pro
305                 310                 315                 320

Leu Leu Thr Ala Asp Glu Ile Lys Pro Thr Ile Lys Glu Leu Val Met
                325                 330                 335

Ala Ala Pro Asp Asn Pro Ser Asn Ala Val Glu Trp Ala Met Ala Glu
            340                 345                 350

Met Val Asn Lys Pro Glu Ile Leu Arg Lys Ala Met Glu Glu Ile Asp
    355                 360                 365

Arg Val Val Gly Lys Glu Arg Leu Val Gln Glu Ser Asp Ile Pro Lys
370                 375                 380

Leu Asn Tyr Val Lys Ala Ile Leu Arg Glu Ala Phe Arg Leu His Pro
385                 390                 395                 400

Val Ala Ala Phe Asn Leu Pro His Val Ala Leu Ser Asp Ala Thr Val
                405                 410                 415

Ala Gly Tyr His Ile Pro Lys Gly Ser Gln Val Leu Leu Ser Arg Tyr
            420                 425                 430

Gly Leu Gly Arg Asn Pro Lys Val Trp Ala Asp Pro Leu Ser Phe Lys
        435                 440                 445

Pro Glu Arg His Leu Asn Glu Cys Ser Glu Val Thr Leu Thr Glu Asn
    450                 455                 460

Asp Leu Arg Phe Ile Ser Phe Ser Thr Gly Xaa Arg Gly Cys Ala Ala
```

```
465                 470                 475                 480
Pro Ala Leu Gly Thr Ala Leu Thr Thr Met Leu Leu Ala Arg Leu Leu
                485                 490                 495
Gln Gly Phe Thr Trp Lys Leu Pro Glu Asn Glu Thr Arg Val Glu Leu
            500                 505                 510
Met Glu Ser Ser His Asp Met Phe Leu Ala Lys Pro Leu Val Met Val
        515                 520                 525
Gly Glu Leu Arg Leu Pro Glu His Leu Tyr Pro Thr Val Lys
    530                 535                 540
```

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 18:

```
Lys Pro Glu Arg His Leu
1               5
```

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 19:

```
Thr Gly Lys Arg Gly Cys
1               5
```

(2) INFORMATION FOR SEQ ID NO: 20:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 20:

```
Lys Pro Glu Arg His Leu Asn Glu Cys Ser Glu Val Thr Leu Thr Glu
1               5                   10                  15
```

```
Asn Asp Leu Arg Phe Ile Ser Phe Ser Thr Gly Lys Arg Gly Cys
            20                  25                  30
```

(2) INFORMATION FOR SEQ ID NO: 21:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 21:

```
Lys Pro Glu Arg His Phe Asn Glu Cys Ser Glu Val Thr Leu Thr Glu
1               5                  10                  15
Asn Asp Leu Arg Phe Ile Ser Phe Ser Thr Gly Lys Arg Gly Cys
            20                  25                  30
```

(2) INFORMATION FOR SEQ ID NO: 22:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 22:

```
Gly Leu Val Lys Glu Gly Val Asp Met Glu Glu Gly Thr Leu
1               5                  10
```

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 23:

```
Met Gly Leu Val Lys Glu Gly Val Asp Met Glu Glu Gly Thr Leu
1               5                  10                  15
```

CYTOCHROME P450 MONOOXYGENASES

This is a divisional of U.S. patent application Ser. No. 09/380,420, filed Nov. 12, 1999 and now U.S. Pat. No. 6,300,544, which is a §371 of PCT/EP98/01253, filed Mar. 5, 1998, and published Sep. 17, 1998, as WO 98/40470, which claims priority of European Patent Application No. 97810132.7, filed Mar. 7, 1997, and European Patent Application No. 97810954.4, filed Dec. 8, 1997.

The present invention relates to genetic engineering in plants using recombinant DNA technology in general and to enzymes involved in the biosynthesis of cyanogenic glycosides and genes encoding these enzymes in particular. The proteins and genes according to the invention can be used to improve the nutritive value or pest resistance of plants.

Cyanogenic glycosides constitute secondary plant metabolites in more than 2000 plant species. In some instances they are the source of HCN which can render a plant toxic if it is taken as food. For example the tubers of the cyanogenic crop cassava (*Manihot esculenta*) constitute an important staple food in tropical areas. The cyanogenic glycosides present in the tubers may cause cyanide poisoning in humans due to insufficiently processed cassava products. Other plant species whose enzymatic production of HCN accounts for their potential toxicity if taken in excess as food or used as animal feed include white clover (*Trifolium repens*), sorghum (*Sorghum bicolor*), linen flax (*Linum usitatissimum*), triglochinin (*Triglochin maritima*), lima beans (*Phaseolus lunatus*), almonds (Amygdalus) and seeds of apricot (Prunus), cherries and apple (Malus). The toxic properties could be reduced by blocking the biosynthesis of cyanogenic glycosides in these plants.

The primary precursors of the naturally occuring cyanogenic glycosides are restricted to the five hydrophobic protein amino acids valine, leucine, isoleucine, phenylalanine and tyrosine and to a single non-protein amino acid, cyclopentenylglycine. These amino acids are converted in a series of reactions to cyanohydrins which are ultimately linked to a sugar residue. Amygdalin for example constitutes the O-β-gentiobioside and prunasin the O-β-glucoside of (R)-mandelonitrile. Another example of cyanogenic glycosides having aromatic aglycones is the epimeric pair of the cyanogenic glycosides dhurrin and taxiphyllin which are to be found in the genus Sorghum and Taxus, respectively. p-Hydroxymandelonitrile for example is converted into dhurrin (β-D-glucopyranosyloxy-(S)-p-hydroxy-mandelonitrile) by a UDPG-glycosyltransferase. Similiar glycosyltransferases are believed to be present in most plants. Vicianin and lucumin are further examples for disaccharide derivatives similiar to amygdalin. Sambunigrin contains (S)-mandelonitrile as its aglycone and is therefore epimeric to prunasin. Examples of cyanogenic glycosides having aliphatic aglycones are linamarin and lotaustralin found in clover, linen flax, cassava and beans. A detailed review on cyanogenic glycosides and their biosynthesis can be found in Conn, Naturwissenschaften 66:28–34, 1979, herein incorporated by reference.

The biosynthetic pathway for the cyanogenic glucoside dhurrin derived from tyrosine has been extensively studied (Halkier et al, 'Cyanogenic glucosides: the biosynthetic pathway and the enzyme system involved' in: 'Cyanide compounds in biology', Wiley Chichester (Ciba Foundation Symposium 140), pages 49–66, 1988; Halkier and Moller, Plant Physiol. 90:1552–1559, 1989; Halkier et al, The J. of Biol. Chem. 264:19487–19494, 1989; Halkier and Moller, Plant Physiol. 96:10–17, 1990, Halkier and Moller, The J. of Biol. Chem. 265:21114–21121, 1990; Halkier et al, Proc. Natl. Acad. Sci. USA 88:487–491, 1991; Sibbesen et al, in: 'Biochemistry and Biophysics of cytochrome P450. Structure and Function, Biotechnological and Ecological Aspects', Archakov, A. I. (ed.), 1991, Koch et al, 8th Int. Conf. on Cytochrome P450, Abstract PII.053; and Sibbesen et al, 8th Int. Conf. on Cytochrome P450, Abstract PII.016). L-Tyrosine is converted to p-hydroxy-mandelonitrile (the precursor of dhurrin), with N-hydroxytyrosine, N,N-dihydroxytyrosine, (E)- and (Z)-p-hydroxyphenylacetaldehyd oxime, and p-hydroxyphenylacetonitrile being intermediates. Two monooxygenases of the cytochrome P450 type are involved in this pathway. In cassava a similiar pathway involving cytochrome P450 dependent monooxygenases is used for the synthesis of linamarin and lotaustralin from valine and isoleucine, respectively (Koch et al, Archives of Biochemistry and Biophysics, 292:141–150, 1992). The complex pathway from L-tyrosine to p-hydroxymandelonitrile in *Sorghum bicolor* was demonstrated to require two multi-functional cytochrome P450 dependent monooxygenases only. The first enzyme, designated $P450_{TYR}$, converts tyrosine to p-hydroxyphenylacetaldehyd oxime. The second enzyme, designated $P450_{OX}$, converts the aldoxime to p-hydroxy-mandelonitrile. In view of the similiarities between the biosynthetic pathways of cyanogenic glucosides in different plants it is generally assumed that said pathways involve two multifunctional P450 dependent monooxygenases, $P450_I$ and $P450_{II}$, which convert the precursor amino acid to the corresponding aldoxime and the aldoxime to the corresponding cyanohydrin, respectively. $P450_I$ is a specific enzyme which determines the substrate specificity and, thus, the type of glucoside produced, whereas $P450_{II}$ is expected to be less specific in converting a range of structurally different aldoximes into the corresponding cyanohydrin. Glucosinolates are hydrophilic, non-volatile thioglycosides found within several orders of dicotyledoneous angiosperms (Cronquist, 'The Evolution and Classification of Flowering Plants, New York Botanical Garden, Bronx, 1988). The occurance of cyanogenic glucosinolates and glucosides is mutually exclusive. The greatest economic significance of glucosinolates is their presence in all members of the Brassicaceae (order of Capparales), whose many cultivars have for centuries provided mankind with a source of condiments, relishes, salad crops and vegetables as well as fodders and forage crops. More recently, rape (especially *Brassica napus* and *Brassica campestris*) has emerged as a major oil seed of commerce. About 100 different glucosinolates are known possessing the same general structure but differing in the nature of the side chain. Glucosinolates are formed from protein amino acids either directly or after a single or multiple chain extension (Underhill et al, Biochem. Soc. Symp. 38:303–326, 1973). N-hydroxy amino acids and aldoximes which have been identified as intermediates in the biosynthesis of cyanogenic glycosides also serve as efficient precursors for the biosynthesis of glucosinolates (Kindl et al, Phytochemistry 7:745–756, 1968; Matsuo et al, Phytochemistry 11:697–701, 1972; Underhill, Eur. J. Biochem. 2:61–63, 1967). Cytochrome $P450_I$ involved in cyanogenic glycoside synthesis is thus functionally very similiar to the corresponding biosynthetic enzyme in glucosinolate synthesis, and is therefore expected to be a member of the same family of P450 enzymes. Thus we have isolated a cDNA clone from *Sinapis alba* encoding a P450 enzyme (SEQ ID NO:17) with 54% identity to $P450_{TYR}$ (CYP79) and catalyzing the first step in the biosynthesis of glucosinolates, that is the formation of the aldoxime from the parent amino acid. This cDNA clone shows approximately 90% identity to an Aribidopsis EST sequence (T42902) which strongly indicates that this cytochrome P450 enzyme is highly conserved in glucosinolate containing species.

The reduction of the complex biosynthetic pathway for cyanohydrins described above to the catalytic activity of only two enzymes, cytochrome $P450_I$ and $P450_{II}$, allows for the manipulation of the biosynthetic pathway of cyanogenic glucosides in plants. By transfection of gene constructs coding for one or both of the monooxygenases a biosynthetic pathway for cyanogenic glucosides can either be modified, reconstituted, or newly established.

The modification or introduction of a biosynthetic pathway for cyanogenic glycosides in plants by methods known in the art is of great interest, since cyanogenic glycosides can be toxic to insects, acarids, and nematodes. Therefore, the modification, introduction or reconstitution of a biosynthetic pathway for cyanogenic glycosides in plants or certain plant tissues will allow to render plants unpalatable for insects, acarids or nematodes and thus help to reduce the damage to the crop by pests. In combination with other insecticidal principles such as *Bacillus thuringiensis* endotoxins the damage to the crop by pests could be even further reduced.

Alternatively, the sequences of the genes encoding the monooxygenases according to the invention can be used to design DNA plasmids which upon transfection into a plant containing cyanogenic glycosides such as cassava, sorghum or barley, eliminate cyanogenic glycosides normally produced in wildtype plants. This can be achieved by expression of antisense or sense RNA or of ribozymes as described in EP-458367-A1, EP-240208-A2, U.S. Pat. No. 5,231,020, WO89/05852, and WO90/11682 which inhibits the expression of monooxygenases according to the invention. This is of great interest as in spite of numerous efforts it has not been possible through traditional plant breeding to completely remove the cyanogenic glycosides from for example cassava or sorghum. On the other hand it has been shown that elevated amounts of cyanogenic glycosides in the epidermal cells of barley cultivars confer increased sensitivity to attack by the mildew fungus *Erysiphe graminis* (Pourmohensi, PhD thesis, Göttingen, 1989; Ibenthal et al, Angew. Bot. 67:97–106, 1993). A similiar effect has been observed in the cyanogenic rubber tree *Hevea brasiliensis* upon attack by the fungus *Microcyclus ulei* (Lieberei et al, Plant Phys. 90:3–36, 1989) and with flax attacked by *Colletotrichum lini* (Lüdtke et al, Biochem. Z. 324:433–442, 1953). In these instances the quantitative resistance of the plants stipulated above and of other plants, where cyanogenic glycosides confer increased sensitivity to attack by microorganisms, can be increased by preventing the production of cyanogenic glycosides in such plants. In barley, the cyanogenic glycosides are located in the epidermal cells. The expression of antisene, sense or ribozyme constructs is therefore preferably but not necessarily driven by an epidermis specific promoter.

The presence of even minor amounts of cyanogenic glycosides in plants may also cause nutritional problems due to generation of unwanted carcinogens as demonstrated in barley. Barley malt for example contains low amounts of the cyanogenic glucoside epiheterodendrin which in the cause of production of grain-based spirits can be converted to ethylcarbamate which is considered to be a carcinogen. Attempts are being made to introduce mandatory maximum allowable concentrations of ethylcarbamate in fermented food, beverages and spirits (Food Chemical News 29:33.35, 1988).

WO 95/16041 describes a DNA molecule coding for a cytochrome $P450_I$ monooxygenase, which catalyzes the conversion of an amino acid to the corresponding N-hydroxyamino acid, N,N-dihydroxyamino acid, and the conversion of the N,N-dihydroxyamino acid to the corresponding aldoxime. The parent amino acid is selected from the group consisting of tyrosine, phenylalanine, tryptophan, valine, leucine, isoleucine and cyclopentenylglycine. The DNA molecules either correspond to naturally occuring genes or to functional homologues thereof which are the result of mutation, deletion, truncation, etc. but still encode a cytochrome $P450_I$ monooxygenase capable of catalyzing more than one reaction of the biosynthetic pathway of cyanogenic glycosides. The monooxygenases preferably contain a single catalytic center.

Additionally WO 95/16041 describes DNA molecules coding for cytochrome $P450_{II}$ monooxygenases such as $P450_{OX}$ of *Sorghum bicolor* (L.) Moench. They catalyze the conversion of an aldoxime to a nitrile and the conversion of the nitrile to the corresponding cyanohydrin. The catalysis of the conversion of tyrosine into p-hydroxyphenylacetonitrile by two multifunctional P450 enzymes explains why all intermediates in this conversion except (Z)-p-hydroxyphenylacetaldoxime are channelled. The strategy suggested for the isolation of $P450_{OX}$ is based on that used for the isolation of $P450_{TYR}$ (CYP79, Sibbesen et al, Proc. Natl. Acad Sci. USA 91: 9740–9744, 1994) from sorghum. In this approach a DEAE Sepharose ion exchange column serves to bind P450 enzymes whereas the yellow pigments in the sample do not bind. Removal of the pigments serves a dual purpose. It is a prerequisite for binding of P450 enzyms to the subsequent columns, and it enables assessment of the content of P450 by spectrometry (carbon monoxide and substrate binding). The present invention demonstrates that $P450_{OX}$ in contrast shows a low binding affinity to the DEAE column and is essentially recovered in the run through and wash fractions. To separate $P450_{OX}$ activity from the yellow pigments by a Triton X-114 based phase partitioning procedure is applied. Using preferentially 0.6 to 1% Triton X-114, $P450_{OX}$ is found to partition to both phases in contrast to $P450_{TYR}$, which is recovered in the detergent rich upper phase. By increasing the concentration of Triton X-114 up to 6%, the majority of $P450_{OX}$ is recovered from the detergent poor lower phase, while the yellow pigments are present in the upper phase. A disadvantage of using 6% Triton X-114 is an enhancement of the conversion of $P450_{OX}$ into its denatured P420 form. This knowledge is used in the present invention to purify for the first time $P450_{II}$ monooxygenases such as $P450_{OX}$, to clone the genes encoding the monooxygenases, and to stably transform plants with the monooxygenase encoding genes. The isolation of $P450_{OX}$ and determination of partial amino acid sequences permit the design of oligonucleotide probes and the isolation of a cDNA encoding $P450_{OX}$. However, in the present case cloning was accomplished via an independent approach.

The invention relates primarily to DNA molecules encoding cytochrome $P450_{II}$ monooxygenases, which catalyze the conversion of an aldoxime to a nitrile and the conversion of said nitrile to the corresponding cyanohydrin. Preferably the aldoxime is the product of a conversion of an amino acid selected from the group consisting of tyrosine, phenylalanine, tryptophan, valine, leucine, isoleucine and cyclopentenylglycine or an amino acid selected from the group consisting of L-tyrosine, L-valine and L-isoleucine, catalyzed by a $P450_I$ monooxygenase as described in WO 95/16041. The DNA molecules according to the invention either correspond to naturally occuring genes or to homologues thereof which are the result of mutation, deletion, truncation, etc. but still encode a cytochrome $P450_{II}$ monooxygenase, which catalyzes the conversion of an aldoxime to a nitrile and the subsequent conversion of said nitrile to the corresponding cyanohydrin. The monooxygenases according to the invention catalyze more than one reaction of the biosynthetic pathway of cyanogenic glycosides and preferably contain a single catalytic center.

Cytochrome $P450_{II}$ enzymes might be present in most living organisms. The DNA molecules according to the present invention encoding $P450_{II}$ monooxygenases are structurally and functionally similar to DNA molecules obtainable from various plants which produce cyanogenic glycosides. In a preferred embodiment of the invention the DNA molecules hybridize to a fragment of the DNA molecule with the nucleotide sequence given in SEQ ID NO:1. Said fragment is more than 10 nucleotides long and preferably longer than 15, 20, 25, 30, or 50 nucleotides. Factors that affect the stability of hybrids determine the stringency of hybridization conditions and can be measured in dependence of the melting temperature $T_m$ of the hybrids formed. The calculation of $T_m$ is desribed in several textbooks. For example Keller et al describe in: "DNA Probes: Background, Applications, Procedures", Macmillan Publishers Ltd, 1993, on pages 8 to 10 the factors to be considered in the calculation of $T_m$ values for hybridization reactions. The DNA molecules according to the present invention hybridize with a fragment of SEQ ID NO:1 at a temperatur 30° C. below the calculated $T_m$ of the hybrid to be formed. Preferably they hybridize at temperatures 25, 20, 15, 10, or 5° C. below the calculated $T_m$.

For the purposes of gene manipulation using recombinant DNA technology the DNA molecule according to the invention may in addition to the gene coding for the monooxygenase comprise DNA which allows for example replication and selection of the inventive DNA in microorganisms such as E. coli, Bacillus, Agrobacterium, Streptomyces or yeast. It may also comprise DNA which allows the monooxygenase genes to be expressed and selected in homologous or heterologous plants. Such sequences comprise but are not limited to genes the codon usage of which has been adapted to the codon usage of the heterologous plant as described in WO93/07278; to genes conferring resistance to neomycin, kanamycin, methotrexate, hygromycin, bleomycin, streptomycin, or gentamycin, to aminoethylcystein, glyophosphate, sulfonylurea, or phosphinotricin; to scorable marker genes such as galactosidase; to its natural promoter and transcription termination signals; to promoter elements such as the 35S and 19S CaMV promoters, or tissue specific plant promoters such as promoters specific for root (described for example in EP-452269-A2, WO91/13992, U.S. Pat. No. 5,023,179), green leaves such as the maize phosphoenol pyruvate carboxylase (PEPC), pith or pollen (described for example in WO93/07278), or inducible plant promoters (EP-332104); and to heterologous transcription termination signals.

The present invention also relates to the $P450_{II}$ monooxygenases which catalyze the conversion of an aldoxime to a nitrile and the conversion of said nitrile to the corresponding cyanohydrine. In a preferred embodiment of the invention the monooxygenases are purified and can be used to establish monoclonal or polyclonal antibodies which specifically bind to the monooxygenases. In particular cytochrome $P450_{OX}$ having a molecular weight of 55 kD as determined by SDS-PAGE is isolated from Sorghum bicolor (L.) Moench. Its amino acid sequence is given in SEQ ID NO:2.

The catalytic properties of $P450_{OX}$ resembles those of a cytochrome P450 activity reported in microsomes from rat liver (DeMaster et al, J. Org. Chem. 5074–5075, 1992). A characteristic of cytochrome $P450_{OX}$ and of other members belonging to the cytochrome $P450_{OX}$ family is that dehydration of the aldoxime to the corresponding nitrile is dependent on the presence of NADPH but that this dependence in some cases can be overcome by the addition of sodium dithionite or other reductants.

Of all known sequences for cytochrome P450 enzymes, cytochrome $P450_{OX}$ shows the highest amino acid sequence identity (44%) to the avocado enzyme CYP71A1 and less than 40% identity to all other members of the CYP71 family. Avocados, do not produce cyanogenic glycosides and CYP71A1 does not catalyze the conversion of an aldoxime to a nitrile and the conversion of said nitrile to the corresponding cyanohydrin. Thus, according to the present invention a family of cytochrome $P450_{II}$ monooxygenases can be defined the members of which catalyze the conversion of an aldoxime to the corresponding cyanohydrin and have a 40% or higher amino acid sequence identity to that of cytochrome $P450_{OX}$. Preferably the amino acid sequence identity with cytochrome $P450_{OX}$ is higher than 50% or higher than 55%. It is suggested to assign $P450_{OX}$ the first member of a new CYP71 subfamily (CYP71E1) as it clusters with other CYP71 sequences in dendrograms, the graphical output of a multiple sequence alignment. Generally, according to the nomenclature commitee, less than 40% sequence identity on the amino acid level is required for a cytochrome P450 to be assigned to a new CYP family and sequences that are more than 55% identical are assigned to the same subfamily. When making multiple sequence alignments not only sequence identities but also sequence similarities such as same net charge or a comparable hydrophobicity/hydrofilicity of the individual amino acids are considered. In such alignments $P450_{OX}$ clusters with the other CYP71 sequences and should therefore be included in the CYP71 family despite the fact that it shows less than 40% identity to all other members of the CYP71 family except CYP71A1 from avocado. As it shows low sequence identity to the other members it ought to be assigned to a new subfamily. The other CYP71 family members are all from non-cyanogenic species and their function is unknown. The catalytic properties of the previously identified P450s belonging to the CYP71 family remain elusive. They are thought to be involved in terpene hydroxylations. None of them has been suggested to utilize oximes as substrates nor to be multifunctional converting aldoximes into nitriles and cyanohydrins.

A further embodiment of the present invention is to be seen in a method for the preparation of cDNA coding for a cytochrome $P450_{II}$ monooxygenase, which catalyzes the conversion of an aldoxime to a nitrile and the conversion of said nitrile to the corresponding cyanohydrin. It comprises (a) isolating and solubilizing microsomes from plant tissue producing cyanogenic glycosides, (b) purifying the cytochrome P450 monooxygenase, (c) raising antibodies against the purified monooxygenase, (d) probing a cDNA expression library of plant tissue producing cyanogenic glycosides with said antibody, and (e) isolating clones which express the monooxygenase.

Microsomes can be isolated from plant tissues which show a high activity of the enzyme system responsible for biosynthesis of the cyanogenic glycosides. These tissues may be different from plant species to plant species. A preferred source of microsomes are freshly isolated shoots harvested 1 to 20 days, preferably 2 to 10 days and most preferably 2 to 4 days after germination. Etiolated seedlings are preferred from plant producing cyanogenic glycosides but light grown seedlings may also be used. Following isolation the microsomes are solubilized in buffer containing one or more detergents. Preferred detergents are RENEX 690 (J. Lorentzen A/S, Kvistgard, Denmark), reduced Triton X-100 (RTX-100), Triton X-114, and CHAPS.

The cytochrome P450 monooxygenases can be purified applying standard techniques for protein purification such as ultracentrifugation, fractionated precipitation, dialysis, SDS-PAGE and column chromatography. Possible columns comprise but are not limited to ion exchange columns such as DEAE Sepharose, Reactive dye columns such as Cibacron yellow 3 agarose, Cibacron blue agarose and Reactive red 120 agarose, and gel filtration columns such as Sephacryl S-1000. The cytochrome P450 content of the individual fractions can be determined from carbon monoxide difference spectra. A special difficulty during the isolation of $P450_{OX}$ which also renders quantification of $P450_{OX}$ difficult is its co-migration with yellow pigments during the initial purification steps instead of binding to the ion exchange column normally used for purification of P450 enzymes such as for example $P450_{TYR}$. The presence of yellow pigments prevents the binding of $P450_{OX}$ to a number of different column materials and thus constitutes a major obstacle towards further purification. Separation of $P450_{OX}$ from the yellow pigments could, however, be accomplished by temperature induced Triton X-114 phase partitioning. The method was optimized with respect to $P450_{OX}$ recovery and removal of pigments by increasing the amount of Triton X-114. At 6%, which is six to ten fold the level used for other P450s, approximately 80% of the $P450_{OX}$ activity partitions to the clear lower phase. Little purification besides the removal of yellow pigments is achieved in this purification step. However, when the $P450_{OX}$ containing lower phase is applied to a Cibacron blue dye column, salt gradient elution produced nearly homogeneous $P450_{OX}$ as judged from the presence of a major Coomassie stained band with an apparent molecular mass of 55 kDa in those fractions which by reconstitution showed $P450_{OX}$ activity. Isolated $P450_{OX}$ produced a carbon monoxide spectrum with an absorption peak at 450 nm but a relatively large part of the isolated enzyme was present in the denatured P420 form. Quantitative determination of the total content and specific activity of $P450_{OX}$ at the different steps in the isolation procedure was hampered by the continuous conversion of $P450_{OX}$ into the denatured P420 form. In addition, the specific activity of $P450_{OX}$ is dependent on the inhibitory effects exerted by the different detergents used. The total P450 content of the fractions is thus to be considered semiquantitative.

The purified proteins can be used to elicit antibodies in for example mice, goats, sheeps, rabbits or chickens upon injection. 5 to 50 µg of protein are injected several times during approximately 14 day intervals. In a preferred embodiment of the invention 10 to 20 µg are injected 2 to 6 times in 14 day intervals. Injections can be done in the presence or absence of adjuvants. Immunoglobulins are purified from the antisera and spleens can be used for hybridoma fusion as described in Harlow and Lane, 'Antibodies: A Laboratory Manual', Cold Spring Harbor Laboratory, Cold Spring Harbor, N.Y., 1988, herein incorporated by reference. Antibodies specifically binding to a cytochrome $P450_{II}$ monooxygenase can also be used in plant breeding to detect plants producing altered amounts of cytochrome P450 monooxygenases and thus altered amounts of cyanogenic glycosides.

The methods for the preparation of plant tissue cDNA libraries are extensively described in Sambrook et al, Molecular cloning: A laboratory manual. Cold Spring Harbor Laboratory Press, Cold Spring Harbor, N.Y., 1989, the essential parts of which regarding preparation of cDNA libraries are herein incorporated by reference. PolyA$^+$ RNA is isolated from plant tissue which shows a high activity of the enzyme system responsible for biosynthesis of the cyanogenic glycosides. These tissues may be different from plant species to plant species. A preferred tissue for polyA$^+$ RNA isolation is the tissue of freshly isolated shoots harvested 1 to 20 days, preferably 2 to 10 days and most preferably 2 to 4 days after germination. The obtained cDNA libraries can be probed with antibodies specifically binding the cytochrome $P450_{II}$ monooxygenase and clones expressing the monooxygenase can be isolated.

An alternative method for the preparation of cDNA coding for a cytochrome $P450_{II}$ monooxygenase comprises (a) isolating and solubilizing microsomes from plant tissue producing cyanogenic glycosides, (b) purifying the cytochrome $P450_{II}$ monooxygenase, (c) obtaining a complete or partial protein sequence of the monoxygenase, (d) designing oligonucleotides specifying DNA coding for 4 to 15 amino acids of said monooxygenase protein sequence (e) probing a cDNA library of plant tissue producing cyanogenic glycosides with said oligonucleotides, or DNA molecules obtained from PCR amplification of cDNA using said oligonucleotides, and (f) isolating clones which encode cytochrome $P450_{II}$ monooxygenase.

Amino acid sequences of internal peptides which are the result of protease digestion can be obtained by standard techniques such as Edman degradation. Oligonucleotides specifying DNA coding for partial protein sequences of the inventive monooxygenases are obtained by reverse translation of parts of the protein sequence according to the genetic code. Protein sequences encoded by DNA sequences of low degeneracy are preferred for reverse translation. Their length ranges from 4 to 15 and preferably from 5 to 10 amino acids. If necessary the codons used in the oligonucleotides can be adapted to the codon usage of the plant source (Murray et al, Nucleic Acids Research 17:477–498, 1989). The obtained oligonucleotides can be used to probe cDNA libraries as described in Sambrook et al, (Molecular cloning: A laboratory manual. Cold Spring Harbor Laboratory Press, Cold Spring Harbor, N.Y., 1989) for clones which are able to basepair with said oligonucleotides. Alternatively, oligonucleotides can be used in a polymerase chain reaction, the methodology of which is known in the art, with plant cDNA as the template for amplification. In this case the obtained amplification products are used to probe the cDNA libraries. Clones encoding cytochrome $P450_{II}$ monooxygenases are isolated.

An alternative method of cloning genes is based on the construction of a gene library composed of expression vectors. In that method, analogously to the methods already described above, genomic DNA, but preferably cDNA, is first isolated from a cell or a tissue capable of expressing a $P450_{II}$ monooxygenase and is then spliced into a suitable expression vector. The gene libraries so produced can then be screened using suitable means, preferably antibodies. Clones which comprise the desired gene or at least part of the gene as an insert are selected.

Alternatively, cDNA molecules coding for a cytochrome P450 monooxygenase which catalyzes conversion of an aldoxime to a nitrile and conversion of said nitrile to the corresponding cyanohydrin; can be achieved by (a) designing degenerated oligonucleotides covering 3 to 10 amino acids of conserved regions of A-type cytochromes, (b) using the degenerated oligonucleotides to amplify one or more cytochrome specific DNA fragments using the polymerase chain reaction, (c) screening a cDNA library with the cytochrome specific fragments to obtain full length cDNA, (d) expressing the full length cDNA in a microbial host, (e) identifying hosts expressing cytochrome P450 monooxygenase which catalyzes the conversion of an aldoxime to a nitrile and the conversion of said nitrile to the corresponding cyanohydrin, and (f) purifying the cloned DNA from said host.

Total DNA from a DNA library, preferably from a cDNA library, can be used as template in a PCR reaction with one or more primers representing conserved regions of A-type cytochromes (Durst et al, Drug Metabolism and Drug Interactions 12: 189–206, 1995) which are believed to be derived from a common plant cytochrome P450 ancestor. Based on a multiple sequence alignment of A-type cytochromes P450 three highly conserved regions on the amino acid level can be defined: region 1 (V/I)KEX(L/F)R, region 2 FXPERF, and region 3 PFGXGRRXCXG. Degenerate inosine (I) containing primers can be designed each covering 3 to 10 and preferably about 5 or 6 amino acids of the two regions respectively. PCR is for example performed in three consecutive rounds. Round 1 using a primer covering the consensus region FXPERF and a standard T7 primer covering the T7 promoter in the library vector amplifies cDNAs derived from mRNAs encoding A-type cytochromes P450. A second round of PCR using primers covering the two consensus regions and the amplified DNA of round 1 as template preferentially amplifies a 100 bp fragment which is then ligated into pBluescript and sequenced. Gene specific primers are designed based on the DNA sequence obtained. They are used in round 3 in combination with a primer complementary to the poly A tail (primer dT+V) and DNA of PCR round 1 as the template to amplify an approximately 500 bp DNA fragment which can be used as a gene specific probe to isolate full-length cDNAs. This PCR approach is not unique to the isolation of $P450_{OX}$ but is general for the isolation of A-type cytochromes P450. The A-type cytochromes P450 obtained need to be heterologously expressed to determine their function.

cDNA clones or PCR products prepared as described above or fragments thereof may be used as a hybridization probe in a process of identifying further DNA sequences encoding a protein product that exhibits $P450_{II}$ monooxygenase activity from a homologous or a heterologous source organism such as fungi or heterologous plants. A suitable source is tissue from plants containing cyanogenic glycosides. Said clones or PCR products may also be used as an RFLP marker to determine, for example, the location of the cytochrome P450 monooxygenase gene or a closely linked trait in the plant genome or for marker assisted breeding [EP-A 306139; WO 89/07647].

Using the methods described above it is possible to isolate various genes that code for a $P450_{II}$ monooxygenase. Said genes can be used in a method for producing a purified recombinant cytochrome $P450_{II}$ monooxygenase which catalyzes the conversion of an aldoxime to a nitrile and the conversion of said nitrile to the corresponding cyanohydrin; comprising (a) engineering the gene encoding said monooxygenase to be expressible in a host organism such as bacteria, yeast or insect cells, (b) transforming said host organism with the engineered gene, and (c) isolating the protein from the host organism or the culture supernatant.

In a preferred embodiment of the invention the method is used to obtain purified recombinant cytochrome $P450_{OX}$, or cytochrome $P450_{OX}$ which has been modified by known techniques of gene technology. Preferably the modifications lead to increased expression of the recombinant protein or to altered substrate specificity.

The inventive DNA molecules can be used to obtain transgenic plants resistant to insects or acarids. Specific embodiments are listed but not limited to those in Table B of WO 95/16041 (page 45) as well as to nematodes described below. For convenience only said Table is not repeated in this specification but it is meant to be incorporated herein by referring to the disclosure of WO 95/16041. Preferably the transgenic plants are resistant to Coleoptera and Lepidoptera such as western corn root worm (*Diabrotica virgifera virgifera*), northern corn root worm (*Diabrotica longicornis barberi*), southern corn rootworm (*Diabrotica undecimpunctata howardi*), cotton bollworm, European corn borer, corn root webworm, pink bollworm and tobacco budworm. Nematodes are the principal animal parasites of plants causing global losses to agriculture estimated at >$100 billion each year. Certain nematodes induce feeding sites involving plant cell modification and feeding at one site for several hours or considerably more. They include species of the genera Meloidogyne Globodera, Heterodera, Rotylenchulus, Tylenchulus, Naccobus, Xiphinema, Longidorus, Paralongidorus, Cryphodera, Trophotylenchulus, Hemicycliophora, Criconemella, Verutus and Heliocotylenchus. Genera considered to feed for a more restricted period at one site include Pratylenchus, Radopholus, Hirschmanniella, Trichodorus, Paratrichodorus, Ditylenchus, Aphelenchoides, Scutellonema, and Belonolaimus.

The transgenic plants comprise DNA coding for the new monooxygenases which catalyze the conversion of said aldoxime to a nitrile and the conversion of said nitrile to the corresponding cyanohydrine. In addition the transgenic plants may comprise monooxygenase genes genetically linked to herbicide resistance genes. The transgenic plants are preferably monocotyledoneous or dicotyledoneous plants. Specific embodiments are listed in Table A of WO 95/16041 (pages 33–44). For convenience only said Table is not repeated in this specification but it is meant to be incorporated herein by referring to the disclosure of WO 95/16041. Preferably they are selected from the group consisting of maize, rice, wheat, barley, sorghum, cotton, soybeans, sunflower, grasses, oil seed rape, sugar beet, broccoli, cauliflower, cabbage, cucumber, sweet corn, daikon, benas, lettuce, melon, pepper, squash, tomato, and watermelon. The plants can be obtained by a method comprising (a) introducing into a plant cell or plant tissue which can be regenerated to a complete plant, DNA comprising a gene expressible in that plant encoding an inventive monooxygenase, and (b) selecting transgenic plants.

Similarly the inventive DNA molecules can be used to obtain transgenic plants expressing anti-sense or sense RNA or ribozymes targeted to the genes of the endogenous $P450_{II}$ monooxygenases. Expression of these molecules in transgenic plants reduces the expression of cytochrome $P450_{II}$ monooxygenases. Such plants show improved disease resistance or nutritive value due to reduced expression of cyanogenic glycosides. The plants can be obtained with a method comprising (a) introducing into a plant cell or tissue which can be regenerated to a complete plant, DNA encoding sense RNA, anti sense RNA or a ribozyme, the expression of which reduces the expression of cytochrome $P450_{II}$ monooxygenases, and (b) selecting transgenic plants.

A number of very efficient processes are available for introducing DNA into plant cells, which processes are based on the use of gene transfer vectors or on direct gene transfer processes.

One possible method of inserting a gene construct into a cell makes use of the infection of the plant cell with *Agrobacterium tumefaciens* and/or *Agrobacterium rhizogenes*, which has been transformed with the said gene construction. The transgenic plant cells are then cultured under suitable culture conditions known to the person skilled in the art, so that they form shoots and roots and whole plants are finally formed.

Within the scope of this invention is the so-called leaf disk transformation using Agrobacterium (Horsch et al, Science 227:1229–1231, 1985). Sterile leaf disks from a suitable target plant are incubated with Agrobacterium cells comprising one of the chimaeric gene constructions according to the invention, and are then transferred into or onto a suitable nutrient medium. Especially suitable, and therefore preferred within the scope of this invention, are LS media that have been solidified by the addition of agar and enriched with one or more of the plant growth regulators customarily used, especially those selected from the group of the auxins consisting of α-naphthylacetic acid, picloram, 2,4,5-trichlorophenoxyacetic acid, 2,4-dichlorophenoxyacetic acid, indole-3-butyric acid, indole-3-lactic acid, indole-3-succinic acid, indole-3-acetic acid and p-chlorophenoxyacetic acid, and from the group of the cytokinins consisting of kinetin, 6-benzyladenine, 2-isopentenyladenine and zeatin. The preferred concentration of auxins and cytokinins is in the range of 0.1 mg/l to 10 mg/l.

After incubation for several days, but preferably after incubation for 2 to 3 days at a temperature of 20° C. to 40° C., preferably from 23° C. to 35° C. and more preferably at 25° C. and in diffuse light, the leaf disks are transferred to a suitable medium for the purpose of shoot induction. Especially preferred for the selection of the transformants is an LS medium that does not contain auxin but contains cytokinin instead, and to which a selective substance has been added. The cultures are kept in the light and are transferred to fresh medium at suitable intervals, but preferably at intervals of one week. Developing green shoots are cut out and cultured further in a medium that induces the shoots to form roots. Especially preferred within the scope of this invention is an LS medium that does not contain auxin or cytokinin but to which a selective substance has been added for the selection of the transformants.

In addition to Agrobacterium-mediated transformation, within the scope of this invention it is possible to use direct transformation methods for the insertion of the gene constructions according to the invention into plant material.

For example, the genetic material contained in a vector can be inserted directly into a plant cell, for example using purely physical procedures, for example by microinjection using finely drawn micropipettes (Neuhaus et al, Theoretical and Applied Genetics 74:363–373, 1987), electroporation (D'Halluin et al, The Plant Cell 4:1495–1505, 1992; WO92/09696), or preferably by bombarding the cells with microprojectiles that are coated with the transforming DNA ("Microprojectile Bombardment"; Wang et al, Plant Molecular Biology 11:433–439, 1988; Gordon-Kamm et al, The Plant Cell 2:603–618, 1990; McCabe et al, Bio/Technology 11:596–598, 1993; Christou et, Plant Physiol. 87:671–674, 1988; Koziel et al, Biotechnology 11: 194–200, 1993). Moreover, the plant material to be transformed can optionally be pretreated with an osmotically active substance such as sucrose, sorbitol, polyethylene glycol, glucose or mannitol.

Other possible methods for the direct transfer of genetic material into a plant cell comprise the treatment of protoplasts using procedures that modify the plasma membrane, for example polyethylene glycol treatment, heat shock treatment or electroporation, or a combination of those procedures (Shillito et al, Biotechnology 3:1099–1103,1985).

A further method for the direct introduction of genetic material into plant cells, which is based on purely chemical procedures and which enables the transformation to be carried out very efficiently and rapidly, is described in Negrutiu et al, Plant Molecular Biology 8:363–373, 1987.

Also suitable for the transformation of plant material is direct gene transfer using co-transformation (Schocher et al, Bio/Technology 4:1093–1096,1986).

The list of possible transformation methods given above by way of example does not claim to be complete and is not intended to limit the subject of the invention in any way.

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pestidice treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphosmethyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods such as the methods exemplified above which are characterized by the use of transgenic plants, transgenic plant material, or transgenic seed according to the present invention.

The following examples further describe the materials and methods used in carrying out the invention and the subsequent results. They are offered by way of illustration, and their recitation should not be considered as a limitation of the claimed invention.

EXAMPLES

Example 1
Preparation of Microsomes

All steps involving the preparation of microsomes are carried out at 4° C. unless otherwise stated. All buffers are degassed by stirring in vacuo and flushed with argon. Seeds of *Sorghum bicolor* (L.) Moench (hybrid SS1000 from AgriPro, Texas, USA) are germinated in the dark for 40 h at 28° C. on metal screens covered with gauze. Microsomes are prepared from approximately 3 cm etiolated seedlings. The seedlings are harvested and homogenized using a mortar and pestle in 2 volumes (v/w) of 250 mM sucrose, 100 mM Tricine (pH 7.9), 2 mM EDTA, and 2 mM DTT. Polyvinylpolypyrrolidone is added (0.1 g/g fresh weight) prior to homogenization. The homogenate is filtered through 22 μm nylon cloth and centrifuged for 10 minutes at 16500×g. The supernatant is centrifuged for 1 hour at 165000×g. The microsomal pellet is resuspended and homogenized in isolation buffer using a Potter-Elvehjem homogenizer fitted with a teflon pestle. After recentrifugation and rehomogenization the homogenate is frozen in liquid nitrogen and stored at −80° C. until use.

Example 2
Enzyme Assays: Determination of Total Cytochrome P450

Quantitative determination of total cytochrome P450 is carried out by difference spectroscopy using an extinction coefficient of 91 $mM^{-1}$ $cm^{-1}$ for the adduct between reduced cytochrome P450 and carbon monoxide ($A_{450-490}$) (Omura et al, J. Biol. Chem. 239:2370–2378, 1964).

Example 3
Purification of Cytochrome $P450_{OX}$

All steps involving the purification of enzyme are carried out at 4° C. unless otherwise stated.

| Buffer A: | Buffer C: |
|---|---|
| 8.9% glycerol | 8.9% glycerol |
| 10 mM $KH_2PO_4/K_2HPO_4$ (pH 7.9) | 40 mM $KH_2PO_4/K_2HPO_4$ (pH 7.9) |
| 0.2 mM EDTA | 5.0 mM EDTA |
| 2.0 mM DTT | 2.0 mM DTT |
| 1.0% (v/v) Renex 690 | 1.0% (w/v) CHAPS |
| 0.05% RTX-100 | |

Buffers are degassed three times by stirring in vacuo before detergent and DTT are added. Between each degassing the buffer is flushed with argon. The ability of different column fractions to metabolize radiolabeled p-hydroxyphenylacetaldoxime is monitored throughout the purification procedure to identify the presence of $P450_{OX}$ in the fractions.

Microsomes (400 mg protein in 20 ml) are diluted to 100 ml with a buffer composed of 8.9% glycerol, 10 mM $KH_2PO_4/K_2HPO_4$ (pH 7.9), 0.2 mM EDTA, 2 mM DTT after which 100 ml of 10 mM $KH_2PO_4/K_2HPO_4$ (pH 7.9), 8.9% glycerol, 0.2 mM EDTA, 2 mM DTT, 0.1% RTX-100 (v/v), 2% Renex is slowly added with constant stirring. After additional stirring for 30 min and subsequent ultracentrifugation at 150000×g for 35 minutes, the approximately 190 ml supernatant are applied with a flow rate of 100 ml/h to a 5×5 cm column of DEAE Sepharose FF/S-100 Sepharose (20/80 wet volumes, Pharmacia) equilibrated in buffer A. The DEAE Sepharose ion exchange resin is diluted with S-100 Sepharose gel filtration material in the ratio 1:4 to avoid too high concentrations of cytochrome P450 enzymes upon binding, which could result in irreversible aggregation. The column is then washed with 150 ml buffer A. $P450_{OX}$ binds weakly to the column and was essentially recovered in those of the run off and wash fractions which contain yellow pigment. Fractions containing $P450_{OX}$, identified by their absorption at 420 nm, their CO binding spectra and their ability to metabolize oxime in reconstitution experiments (see Example 4), are combined (approximately 200 ml). They are used for further purification or can be frozen. The combined $P450_{OX}$ fractions are adjusted during constant stirring to 30% (v/v) glycerol and 6% Triton X-114 by the dropwise addition of appropriate amounts of a mixture of glycerol and Triton X-114. The stirring is continued for 20 min, and is followed by 25 minutes of centrifugation at 24500×g, 25° C., and no brake (temperature induced Triton X-114 phase partitioning). Two phases are formed, a yellow upper phase and a clear lower phase. The lower phase which contains the major part of the cytochrome $P450_{OX}$ activity is collected is diluted 2.5 fold to approximately 350 ml with buffer C and applied with a flow rate of 70 ml/h to a 1.9×5 cm column of Cibacron blue 3GA-agarose equilibrated in buffer C. The column is washed with 50 ml of buffer C and the retained cytochrome P450$_{OX}$ is eluted with approximately 60 ml of a 0–1.5 M KCl linear gradient in buffer C. Teh fractions which by SDS-PAGE show the presence of a single polypeptide band in the 50–60 kDa region are combined and dialyzed under nitrogen for 24 h against 1 l of 8.9% glycerol, 10 mM KH$_2$PO$_4$/K$_2$HPO$_4$ (pH 7.9), 5 mM EDTA, 2 mM DTT (dialysis buffer) to reduce the salt and detergent content. The enzyme preparation is frozen in liquid nitrogen, and stored at −80° C.

Example 4

Characterization of Cytochrome P450$_{OX}$ Obtained by Isolation from Sorghum Microsomes 4.1. Molecular Weight and Amino Acid Sequence Data The molecular weight of P450$_{OX}$ as determined by SDS-PAGE is 55 kD. The protein band corresponding to the P450$_{OX}$ isolated from the Cibacron blue 3GA-agarose column is excised from 8–25% SDS-polyacrylamide gels and electroeluted. The electroeluted protein is digested with endoproteinase Glu-C (protease V8 sequencing grade, 18 h, 23° C.) according to the manufacturer (Boehringer Mannheim) using an approximate 1:100 weight ratio between proteinase and protein. The electroeluted protein and the digested protein sample are subjected to SDS-PAGE, and the protein and fragments transferred to ProBlott membranes (Applied Biosystems). Coomassie stained regions of the membrane are excised and subjected to N-terminal amino acid sequencing on an Applied Biosystems model 470A Sequenator equipped with an on-line model 120A phenylthiohydantoin amino acid analyzer.

N-terminal amino acid sequencing produced two sequences, which could be read independently due to their difference in relative abundance. A database search (BLAST) showed the sequence -GLVKEGVDMEEGTL (SEQ ID NO:22) to differ in only a single position from the N-terminal sequence of the B subunit of the vacuolar ATPase of barley (Hordeum vulgare) which is MGLVKEG-ADMEEGTh (SEQ ID NO:23—accession number L11862). The barley B subunit has a predicted molecular mass of 54 kDa (20). The presence of the B subunit of the vacuolar ATPase as a contaminant in the P450$_{OX}$ preparation was further substantiated by Western blotting which showed a single band at 55 kDa when using a monoclonal antibody raised against the B subunit of the vacuolar ATPase from oat roots provided by Dr. Heven Sze. The B subunit could be depleted from the P450$_{OX}$ preparation by immobilization on antibody coated microtiter wells. This approach permitted unambiguous determination of the N-terminal amino acid sequence of P450$_{OX}$ as -ATTATPQLLGGSVPEQ and in addition provided the sequence of one internal P450$_{OX}$ peptide fragment, MDRLVADLDRAAA. Attempts to remove the residual amounts of the B subunit of the vacuolar ATPase resulted in the formation of carbon monoxide difference spectra in which the 420 nm component representing inactive the denatured P420 form of P450$_{OX}$ was largely increased and in loss or significantly diminished ability to reconstitute the P450$_{OX}$ activity in the fractions obtained. This reflects the immanent lability of P450$_{OX}$. The B subunit of the vacuolar ATPase is not expected to possess any of the catalytic properties associated with P450$_o$x. Accordingly, the presence of the B subunit as a contaminant was accepted in the metabolic studies of P450$_{OX}$ reported below.

N-terminal Sequence:
-- A T T A T P Q L L G G S V P E Q -- (SEQ ID NO: 3)
Internal Sequence:
-- M D R L V A D L D R A A A -- (SEQ ID NO: 4)

4.2. Isolation of the NADPH-P450 Oxidoreductase

The NADPH-P450 oxidoreductase binds to the DEAE-Sepharose FF/S-100-Sepharose column and is eluted by augmenting buffer A with 0.5 M KCl. The reductase is subsequently purified to homogeneity on a column of 2',5'-ADP-Sepharose 4B (Pharmacia) as previously described (Halkier and Moller, Plant Physiol. 96:10–17, 1990) and concentrated to approximately 15 units/ml.

4.3. Preparation of Soluble UDPG Glucosyitransferase

The glucosyltransferase is partially purified by ammonium sulfate fractionation of the centrifugation supernatant obtained during the preparation of microsomes. The glucosyltransferase fraction precipitates between 40% and 60% (NH$_4$)$_2$SO$_4$ and is dissolved in 5 ml of 50 mM Tricine (pH 7.9), 2 mM DTT, and dialyzed against 2 l of the same buffer overnight.

4.4. Reconstitution of Cytochrome P450$_{OX}$ Activity

Reconstitution of the enzyme activity of a microsomal cytochrome P450 is accomplished by inserting the cytochrome P450 enzyme and the corresponding NADPH cytochrome P450 oxidoreductase into lipid micelles. A mixture of lipids can be used but in the case of cytochrome P450$_{OX}$, dilauroylphosphatidylcholine (DLPC) provides the best enzymatic activity. The number of correctly formed complexes of cytochrome P450$_{OX}$ and NADPH cytochrome P450 oxidoreductase are a rate limiting factor. Excess amounts of the oxidoreductase and concentrated enzyme solutions are utilized to ensure a sufficient number of active complexes.

A functionally reconstituted enzyme is obtained using the following components:

| | |
|---|---|
| Cytochrome P450$_{ox}$: | 20 μg/ml in dialysis buffer |
| NADPH cytochrome P450 oxidoreductase purified from Sorghum bicolor: | 100 μg/ml in 50 mM potassium phosphate buffer (pH 7.9) |
| Lipid: | 10 mg/ml dilauroylphosphatidylcholine, sonicated in 50 mM Tricine (pH 7.9) |
| NADPH: | 25 mg/ml in H$_2$O |
| $^{14}$C-oxime, enzymatically produced from [U-$^{14}$C]-L-tyrosine using reconstituted P450$_{TYR}$, and purified on HPLC | 0.01 μCi/μl, 394 mCi/mmol |

5 μl lipid suspension is mixed in an eppendorf tube with 5 μl NADPH cytochrome P450 oxidoreductase (0.075 units), 10 μl of the cytochrome P450$_{OX}$ (approximately 0.4 pmol) solution, and 0.5 μl $^{14}$C-oxime (0.014 μCi/μl, 394 mCi/mmol). The final volume is adjusted to 30 μl using 50 mM Tricine (pH 7.9) and the enzyme reaction is initiated by addition of 1 μl of NADPH solution. Control samples are prepared by either omitting the NADPH cytochrome P450 oxidoreductase or NADPH from the reaction mixture. The tubes are incubated under constant and gentle agitation at 30° C. for 1 h. After incubation the reaction mixtures are applied to silica coated TLC sheets (Silica gel 60 F$_{254}$, Merck) and developed using an ethyl acetate/toluene (1:5 v/v) mixture as mobile phase. The sheets are placed on storage phosphor screens over night and the resultant products, p-hydroxy phenylacetonitrile and p-hydroxybenzaldehyde are visualized using a STORM 840 phosphorimager from Molecular Dynamics.

When reconstituted into lipid micelles cytochrome P450$_{OX}$ catalyzes the conversion of p-hydroxyphenylacetaldehyde oxime to p-hydroxymandelonitrile which dissociates to p-hydroxybenzaldehyde and HCN. This demonstrates that cytochrome $P450_{OX}$ is a multifunctional protein catalyzing both the conversion of p-hydroxyphenylacetaldehyde oxime to p-hydroxyphenylacetonitrile, and the conversion of p-hydroxyphenylacetonitrile to p-hydroxymandelonitrile. $P450_{OX}$ activity is strictly dependent on the presence of NADPH-P450 oxidoreductase and NADPH. Sodium dithionite (10 mM) does not support metabolism of p-hydroxyphenylacetaldoxime. Omission of dialysis of the enzyme prior to reconstitution causes a relative increase in the accumulation of p-hydroxyphenylacetonitrile compared to p-hydroxybenzaldehyde.

4.5. In vitro Reconstitution of the Complete Pathway of Dhurrin Synthesis from its Parent Amino Acid Tyrosine The complete reaction mixtures contain: 3 μl of isolated, recombinant $P450_{TYR}$ (6 pmol, heterologously expressed in E. coli and isolated as in Halkier et al, Arch. Biochem. Biophys. 322: 369–377, 1995), 10 μl of isolated and dialyzed $P450_{OX}$ (approximately 0.4 pmol), 5 μl of NADPH-P450 oxidoreductase (0.075 U), 1 μl of partially purified UDPG glucosyl transferase from Sorghum, 5 μl of DLPC (10 mg/ml in 50 mM $Kp_i$ (pH7)), 0.25 μl of [U-$^{14}$C]-tyrosine (0.05 μCi/mmol, 443 mCi/mmol, Amersham), 3 μl of UDPG (33 mg/ml in 50 mM $Kp_i$ (pH7)), and 3 μl of castanospermin (2 mM in 50 mM $Kp_i$ (pH7)). The components are mixed by repeated suspension and if necessary the final volume adjusted to 30 μl by the use of 50 mM $Kp_i$ (pH7). The enzyme reaction is initiated with 1 μl of NADPH (25 mg/ml). Dhurrin is also synthesized via reconstitution of $P450_{OX}$ with p-hydroxyphenylacetaldehyde oxime (leaving out $P450_{TYR}$ and tyrosine from the reaction mixtures any additional components being unchanged.). These assays contain either 0.5 μl of [U-$^{14}$C]-p-hydroxyphenylacetaldehyd oxime (0.014 μCi/μl, 394 mCi/mmol) or 3 μl of unlabelled p-hydroxyphenylacetaldehyde oxime (20 mM) as substrate for $P450_{OX}$. In the latter case the radioactive label is 1 μl of [U-$^{14}$C]-UDPG (0.025 μCi/μl, 287 mCi/mmol, Amersham). All reaction mixtures are prepared as duplicates. After incubation for 1 h at 30° C. each set of reaction mixtures is applied to TLC sheets. The first set of reaction mixtures is analyzed using the ethyl acetate/toluene solvent as in example 4.5. The second set of reaction mixtures is analyzed using a solvent system consisting of ethyl acetate/acetone/dichloromethane/methanol/water (20/15/6/5/4, v/v/v/v/v) in order to achieve separation of the hydrophilic product dhurrin from tyrosine and from the hydrophobic intermediates. Radiolabelled substrates and products are visualized using the STORM 840-phosphorimager.

The combined use of isolated $P450_{TYR}$ and $P450_{OX}$ in reconstitution experiments with radiolabeled tyrosine as substrate results in the production of p-hydroxyphenylacetonitrile and p-hydroxybenzaldehyde. This demonstrates that $P450_{TYR}$ and $P450_{OX}$ are able to act together in vitro. The p-hydroxyphenylacetaldoxime produced by $P450_{TYR}$ is thus effectively used as a substrate by $P450_{OX}$. No activity was observed in the absence of NADPH-P450 oxidoreductase or in the absence of NADPH. In vitro production of dhurrin using p-hydroxyphenylacetaldoxime as substrate was accomplished by reconstitution of $P450_{OX}$ together with partially purified soluble UDPG glucosyltransferase in the presence of NADPH and UDPG. A cDNA clone from sorghum encoding the UDPG glucosyltransferase which specifically utilizes p-hydroxymandelonitrile as a substrate is not available. Accordingly, in the present study a crude extract of the soluble UDPG glucosyltransferase from sorghum was used to glucosylate p-hydroxymandelonitrile and to demonstrate the in vitro reconstitution of the entire dhurrin biosynthetic pathway. The radiolabeled p-hydroxyphenylacetaldoxime applied was fully metabolized. Castanospermine was added to inhibit the glucosidase activity present in the UDPG glucosyltransferase preparation. In addition to the TLC system used above for separation of hydrophobic compounds, an additional TLC system was introduced for the separation of hydrophilic compounds like dhurrin. The p-hydroxymandelonitrile formed in the reconstitution assay was partly converted to dhurrin as demonstrated by the formation of a radiolabeled compound comigrating with authentic dhurrin. The assignment of this radiolabeled compound as dhurrin was further substantiated by its breakdown in the absence of castanospermine, and by the formation of a comigrating radiolabeled product when the experiment was repeated with radiolabeled UDPG instead of radiolabeled p-hydroxyphenylacetaldoxime. The radiolabeled UDPG unspecifically labeled a range of relatively hydrophilic compounds. Due to the lability of p-hydroxymandelonitrile its conversion to dhurrin is experimentally detected as a disappearance of p-hydroxybenzaldehyde. When radiolabeled p-hydroxyphenyl-acetaldoxime was used as substrate, a number of unidentified, hydrophobic, radiolabeled compounds were produced in addition to dhurrin. The formation of these compounds occurs in the absence of UDPG but requires the presence of the soluble extract, which indicates that the UDPG glucosyltransferase extract contains additional enzymatic activities. Glucosylation of the phenolic group of p-hydroxymandelonitrile would result in the formation of p-glucopyranosyloxymandelonitrile. No radiolabeled product comigrating with an authentic standard of p-glucopyranosyloxymandelonitrile was observed. The glucosidase activity present in the UDPG glucosyltransferase extract was efficiently inhibited by castanospermine.

Upon in vitro reconstitution, the turn-over number of $P450_{TYR}$ (CYP79) is 230 min$^{-1}$ (Sibbesen et al, J. Biol. Chem. 270: 3506–3511, 1995). The partial conversion of $P450_{OX}$ into its denatured P420 form prevents determination of its turn-over number. Using the microsomal system, the $K_m$ and $V_{max}$ values for p-hydroxymandelonitrile production from tyrosine, p-hydroxyphenylacetaldoxime, and p-hydroxyphenylacetonitrile are 0.03, 0.05, and 0.10 mM, and 145, 400, and 50 nmoles mg protein$^{-1}$ h$^{-1}$, respectively (Møller et al, J. Biol. Chem. 254: 8575–8583, 1979).

The entire dhurrin biosynthetic pathway starting from its parent amino acid tyrosine was reconstituted in vitro by combining $P450_{TYR}$, $P450_{OX}$, NADPH-P450 oxidoreductase in DLPC micelles with UDPG glucosyltransferase, tyrosine, NADPH, UDPG, and castanospermine. Tyrosine is converted by $P450_{TYR}$ to p-hydroxyphenylacetaldoxime, which is further converted to p-hydroxyphenylacetonitrile and p-hydroxybenzaldehyde by $P450_{OX}$. Some p-hydroxyphenylacetonitrile accumulates, whereas all the p-hydroxymandelonitrile formed is converted to dhurrin and some unidentified compounds. In this set of experiments, the stoichiometric ratio between $P450_{TYR}$ and $P450_{OX}$ is approximately 15. It is therefore not surprising to detect the accumulation of the p-hydroxyphenylacetaldoxime in the reconstitution assay. The observed accumulation of p-hydroxyphenylacetonitrile is unexpected since previous experiments with sorghum microsomes have shown that p-hydroxyphenylacetonitrile is difficult to accumulate and trap. Partial denaturation or inactivation of the isolated P450$_{OX}$ may explain why p-hydroxyphenylacetonitrile accumulates in the reconstitution experiments with isolated P450$_{OX}$.

4.6. Substrate Binding

The identification of P450$_{OX}$ as a multifunctional enzyme converting p-hydroxyphenylacetaldoxime to p-hydroxymandelonitrile with p-hydroxyphenylacetonitrile as an intermediate stimulated us to investigate the substrate binding ability of P450$_{OX}$. A reverse type I spectrum with an absorption minimum at 381 nm and an absorption maximum at 418 nm was obtained with p-hydroxyphenylacetaldoxime suggesting a shift from a high to a low spin state upon substrate addition. The amplitude increased in size upon incubation and reached a stable maximum after approximately 45 min. No substrate binding spectrum was obtained upon the addition of p-hydroxyphenylacetonitrile.

P450$_{OX}$ was found to be much more labile compared to other P450 enzymes isolated from sorghum. The isolated P450$_{OX}$ produces a reverse Type I substrate binding spectrum upon incubation with p-hydroxyphenylacetaldoxime. The extinction coefficient $E_{420-390}$ corresponding to a complete transition from one spin state to the other is 130 mM$^{-1}$ cm$^{-1}$. In the substrate binding spectra obtained, the maximal amplitudes are approximately twice as large as theoretically calculated even when assuming a complete shift from a high spin to a low spin state. This discrepancy indicates that the P450$_{OX}$ concentration was underestimated when quantified from the 450 nm peak in the carbon monoxide binding spectrum. Alternatively, the P420 form of P450$_{OX}$ is able to bind the oxime and thus contributes to the size of the substrate binding spectrum formed. The latter possibility could explain why maximal amplitudes are only obtained after prolonged incubation.

P450 mediated dehydration of aldoximes to nitriles has previously been reported using liver microsomes (DeMaster et al, J. Org. Chem. 5074–5075, 1992). A major difference between the liver microsomal system and P450$_{OX}$ is that the former requires strict anaerobic conditions whereas the latter proceeds aerobically, catalyzes a subsequent C-hydroxylation reaction, and metabolizes the (e)- as well as the (Z)-isomer. Under anaerobic conditions, a weak Type I spectrum is obtained with the liver microsomes. Upon addition of NADPH or dithionite, a pronounced Soret peak at 442–444 nm is formed. This is concluded to represent the key active species of the P450 in the Fe (II) state. Spectral investigations of P450$_{OX}$ under anaerobic conditions did not disclose the formation of a 442 nm absorbing complex, but the presence of NADPH is required for catalytic activity which indicates that P450$_{OX}$ also needs to be in the Fe (II) state to mediate the dehydration reaction.

Example 5
A-type Cytochrome P450 Probe Generation

PCR was performed on plasmid DNA isolated from a unidirectional plasmid cDNA library (Invitrogen) made from 1–2 cm high etiolated seedlings of Sorghum bicolor (L) Moench using highly degenerated inosine (I) containing primers preferentially selecting for A-type cytochromes P450 (Nelson and Durst, Drug Metabolism and Drug Interactions 12: 189–206 (1995)). Primer 1 (sense strand) with the sequence 5'-GCGGAATTCTTYIIICCNGAR MGNTT-3' (SEQ ID NO:5) covers the consensus amino acid sequence FXPERF (SEQ ID NO:6) where X is any amino acid. Primer 2 (antisense strand) with the sequence 5'-GCGGATCCIIIRCAIIINCKNCKNCC-3' (SEQ ID NO:7) covers the consensus amino acid sequence GRRX-CXG (SEQ ID NO:8). Primer 1 and primer 2 were tailed with EcoRI and BamHI sites, respectively, to ensure that only PCR products generated from both primers were cloned in EcoRI/BamHI digested pBluescript II SK (Strategene). PCR was performed in two consecutive rounds. Round 1 using primer 1 and standard T7 primer 5'-AATACGACTCACTATAG-3' (SEQ ID NO:9) enriches the pool of cDNA encoding A-type cytochromes P450. Round 2 including primer 1 and primer 2 generated predominantly one band of approximately 100 bp specific for A-type cytochromes P450. The PCR reaction for round 1 was set up in a total volume of 100 μl containing 5% DMSO, 200 μM dNTPs, 200 pmol of primer 1, 100 pmol of standard T7 primer, 2.5 units Taq DNA Polymerase in PCR buffer and 1 μl of 100 times diluted plasmid DNA from the cDNA library. The PCR reaction for round 2 was set up in a total of 100 μl containing 5% DMSO, 200 μM dNTPs, 200 pmol of primer 1 and primer 2, 2.5 units Taq DNA Polymerase in PCR buffer and 1 μl of product obtained from PCR round 1. For both rounds of PCR, one cycle of 5 min at 95° C. was followed by 35 cycles of 30 sec at 95° C., 1 min at 50° C., and 30 sec 72° C. The approximate 100 bp product of PCR round 2 was excised from a 2% agarose gel and reamplified prior to cloning into pBluescript. Of the 19 clones sequenced, 10 had very high sequence identity on the amino acid level to cinnamic acid hydroxylase (CYP 74) and were therefore not further studied. Sequence comparisons of the remaining 9 sequences divided these into two groups of 8 and 1 sequences and were denoted "12" and "7", respectively. A sequence "12" gene specific primer located between primer 1 and primer 2: 5'-GCGGATCCGACTACTACGGCTCGC-3' (SEQ ID NO:10) and primer 5'-GCGGATCCTTTTTTTT-TTTTTTTTV-3' (SEQ ID NO:11) both tailed with BamHI were used to amplify a "12" gene specific fragment of approximately 500 bp from PCR round 1 and cloned into pBluescript. Similarly a gene specific fragment for "7" was obtained using the "7" gene specific primer 5'-GCGGATCCGACATCAAGGGCAGCG-3' (SEQ ID NO:12) and primer 5'-GCGGATCCTTTTTTTTTT-TTTTTTV-3'(SEQ ID NO:11). Inserts were labelled with Digoxigenin-11-dUTP (Boehringer Mannheim) by PCR amplification with standard T7 and T3 primers according to the manufacturers instructions and used to screen the cDNA library.

Example 6
Library Screening and DNA Sequencing

All filter hybridizations were done using the DIG system (Boehringer Mannheim). Colony lifts were prepared using nylon membranes (Boehringer Mannheim) and hybridized over night at 68° C. in 5×SSC, 0.1% N-lauroylsarcosine, 0.02% SDS, 1% Blocking Reagent (Boehringer Mannheim). Filters were washed twice for 15 minutes in 0.1×SSC, 0.1% SDS, at 65° C. prior to detection. Full-length clones were obtained for both "12" and "7" as evidenced by sequence analysis. Sequencing was done using the Thermo Sequenase Fluorescent labelled Primer cycle sequencing kit (7-deaza dGTP) (Amersham) and analyzed on an ALF-Express (Pharmacia). Sequence computer analysis was done using the programs in the GCG Wisconsin SequenceAnalysis Package. The full-length cDNA sequence of P450$_{OX}$ and the derived amino acid sequence of the coding region as obtained from nucleotide sequencing of "12" are given in is given in SEQ ID NO: 1 and SEQ ID NO: 2, respectively.

Example 7
Expression in E. Coli

The expression vector pSP19g10L (Barnes, Methods in Enzymology 272: 3–14, 1996) was obtained from Dr. Henry Barnes (Synthetic Genetics/Immune Complex Incorporation, San Diego, Calif.). This plasmid contains the lacZ promoter fused to the short leader sequence of the gene 10 from $T_7$ bacteriophage, g10L, which has been documented as an excellent leader sequence for the expression of various heterologous proteins (Olin et al., 1988). "7" and "12" were modified by PCR using Pwo-polymerase (Boehringer Mannheim) to introduce a NdeI site at the start codon and to change the stop codon to an ochre stop codon immediately followed by a HindIII site. For generation of an expression clone for "7" primer 3 (sense strand) 5'-CGCGGATCCATATGGACGCATCATTACTCCTCTC-CGTCGCGCTC-3'(SEQ ID NO:13) and primer 4 (antisense strand) 5'-CGCAAGCTTATTACATCTCAAC GGGGACCCT-3'(SEQ ID NO:14) were used. Primer 3 introduces silent mutations in codons 3, 4, and 5 to reduce the G/C content around the translation start site and a BamHI site immediately upstream of the NdeI site. The obtained PCR fragment was digested with BamHI and HindIII and ligated into BamHI and HindIII digested pBluescript and controlled by sequencing to exclude PCR errors. Similarly "12" was introduced into pBluescript using primer 5 (sense strand) 5'-CGCGGATCCATATGGCAACAACAGCAA-CCCCGC-AGCTCCTC-3'(SEQ ID NO:15) and primer 6 (antisense strand) 5'-CGCAAGCTTATTATGCT-GCGCGGC GGTTCTTGTATTTGG-3' (SEQ ID NO:16). Primer 5 introduces silent mutations in codons 2, 3, 4, and 5 and primer 6 introduces silent mutations in the last 2 codons to reduce the G/C content. The inserts were cut out using NdeI and HindIII and ligated into NdeI and HindIII digested pSP19g10L. Expression plasmids were transformed into E. coli JM109 cells. Single colonies were grown overnight in LB medium containing 100 mg ampicillin/ml at 37° C., and 5 ml of the overnight culture used to inoculate 500 ml of TB medium containing 50 mg/ml ampicillin, 1 mM thiamine, 1 mM isopropyl -β-thiogalactopyranoside, and 1 mM δ-aminolevulinic acid. Cells were grown at 28° C. for 48 hours at 125 rpm. 1 ml of E. coli transformed with expression constructs of "7", "12", and pSP19g10L were pelleted through centrifugation (2000 g, 10 min), washed and concentrated 10 fold in 50 mM Tricine pH 7.9 and incubated with 14 nCi [U-$^{14}$C] p-hydroxyphenylacetaldehyde oxime with a specific activity of 394 mCi/mmol at 30° C. for 30 min. The incubation mixtures were extracted with ethyl acetat, applied to a TLC plate (Silica gel 60 $F_{254}$, Merck), developed using an ethyl acetate/toluene (1:5 v/v) mixture as mobile phase, and visualized using a STORM 840 from Molecular Dynamics. E. coli transformed with the construct expressing "12" was able to convert p-hydroxyphenylacetaldehyde oxime into p-hydroxyphenylacetonitrile.

CO difference spectra of solubilized spheroblasts of E. coli expressing $P450_{OX}$ contained a major peak at 417 nm and a minor peak at 457 nm. Generally, a CO spectrum with an absorbance peak around 420 nm is indicative of a cytochrome P450 in a non-functional conformation (Imai et al, Eur. J. Biochem. 1: 419–426, 1964). The presence of a major peak at 417 nm suggests that the majority of the expressed cytochrome P450 was present in a non-functional conformation. The apparent shift in absorbance peak from 450 nm to 457 nm may be due to the presence of large amounts of cytochrome P450 in the non-conformational state. Based on the peak at 457 nm, the production was estimated to be 50 nmol of of $P450_{OX}$ per liter E. coli culture per 65 hours.

5 µl membranes isolated as described in Halkier et al, Archives of Biochemistry and Biophysics 322: 369–377, 1995, from E. coli expressing "12" was reconstituted with 0.225 units NADPH-cytochrome P450-reductase, 50 µg NADPH, 42 nCi p-hydroxyphenylacetaldehyde oxime, and 100 µg dilaurylphosphatidylcholine in a total volume of 100 µl of 30 mM Tricine pH 7.9. After incubation at 30° C. for 30 minutes the reaction mixture was applied to a TLC plate and analyzed as described above. Reconstitution of membranes from E. coli expressing "12" resulted in the accumulation of p-hydroxybenzaldehyde which is the stable dissociation product of p-hydroxymandelonitrile, the last intermediate in the biosynthesis of the cyanogenic glucoside dhurrin. This shows that demonstrates that "12" is the cytochrome P450 that catalyzes the conversion of p-hydroxyphenylacetaldehyde oxime to p-hydroxymandelonitrile. The cDNA is designated $P450_{OX}$. A clone comprising the described cDNA of $P450_{OX}$ has been deposited on Jan. 10, 1997 with the DSMZ-Deutsche Sammlung von Mikroorganismen und Zellkulturen GmbH, Mascheroder Weg 1b, D-38124 Braunschweig, under the accession number DSM 11367.

When radioactively labeled phydroxyphenylacetaldoxime was administrated to E. coli cells transformed with $P450_{OX}$, p-hydroxyphenylacetonitrile accumulated in the $P450_{OX}$-expressing E. coli cells. E. coli, which does not contain endogenous cytochromes P450 or a NADPH-cytochrome P450-reductase, has been shown to support the catalytic activity of heterologously expressed cytochromes P450. Two soluble E. coli flavoproteins, flavodoxin and NADPH-flavodoxin reductase, donate the reducing equivalents to the recombinant cytochromes P450. Reconstitution of isolated E. coli membranes or purified recombinant enzyme with sorghum NADPH-cytochrome P450-reductase results in the conversion of p-hydroxyphenylacetaldoxime to p-hydroxymandelonitrile, whereas $P450_{OX}$-expressing E. coli cells metabolize p-hydroxyphenylacetaldoxime to only p-hydroxyphenylacetonitrile. The inability of E. coli to support the conversion of p-hydroxyphenylacetonitrile to p-hydroxymandelonitrile is the first example that the E. coli flavodoxin/NADPH-flavodoxin reductase system is not able to support the catalytic activity of a microsomal cytochrome P450 reaction. Preliminary reconstitution experiments with the membranous and soluble fractions of $P450_{OX}$-expressing E. coli cells have shown that the soluble flavodoxin/NADPH-flavodoxin reductase system only supports $P450_{OX}$ in the conversion of p-hydroxyphenylacetaldoxime to p-hydroxyphenylacetonitrile, and that an inhibitory factor hampering the subsequent hydroxylation reaction is not present in the soluble fraction. The inability of E. coli to support full $P450_{OX}$ activity might reflect the atypical catalytic reactivity of $P450_{OX}$. In E. coli cells transformed with $P450_{OX}$ or with the expression vector a compound with a slightly lower mobility than p-hydroxyphenylacetaldoxime accumulated. This shows that E. coli is able to metabolize p-hydroxyphenylacetaldoxime independent of the presence of $P450_{OX}$.

Example 8

Purification of Recombinant $P450_{OX}$ (CYP71E1)

Spheroblasts from 2 1 E. coli expressing $P450_{OX}$ were were subjected to temperature-induced phase partitioning with 1% Triton X-114 as previously described (Halkier et al, Archives of Biochemistry and Biophysics 322: 369–377, 1995). The $P450_{OX}$ containing upper phase was diluted 100 fold in 10 mM $KP_i$ pH 7.0, 0.05% reduced Triton X-100, 1 mM DTT, 0.5 mM PMSF, the pH adjusted to 7.0 with acetic acid, and applied to a 16 ml fast flow CM-Sepharose column (Pharmacia) equilibrated in buffer D (10 mM $KP_i$ pH 7.0, 0.2% Triton X-114, 0.05% reduced Triton X-100, 10% glycerol, 1 mM DTT, 0.5% PMSF). The column was washed in buffer D and P450$_{OX}$ eluted with a 0–1 M KCl linear gradient (350 ml) in buffer D. The combined P450$_{OX}$ containing fractions (43 ml) were used for the reconstitution experiments and electroeluted recombinant P450$_{OX}$ was used for antibody production in chicken. Purified recombinant P450$_{OX}$ reconstituted with NADPH-cytochrome P450-reductase in DLPC catalyses the conversion of p-hydroxyphenylacetaldehyde oxime to p-hydroxymandelonitrile in the presence of NADPH as described in example 4 section 4.2 for the purification of the plant enzyme.

Example 9

Expression of Dhurrin in Transgenic Arabidopsis and Tobacco 9.1 Construction of Vector Plasmids Three binary vectors for *Agrobacterium tumefaciens* mediated transformation, namely pPZP111.79, pPZP221.71E1, and pPZP111.79.71E1, are generated. For the construction of pPZP111.79 a cDNA clone of P450$_{TYR}$ (WO 95/16041; Koch et al, Arch Biochem Biophys 323:177–186, 1995) is first excised with EcoRI and introduced into the EcoRI site of pRT101 (Kopfer et al, Nucleic Acids Research 15: 5890, 1987) to functionally join the cDNA to the 35S-promoter and a CaMV polyadenylation signal generating plasmid pRT101.79. Prior to the introduction of the P450$_{TYR}$ cDNA a part of the pRT101 polylinker is removed by digestion with SacI and XbaI followed by religation of the blunt-ended ends obtained by Klenow treatment, thus leaving only the EcoRI and XhoI sites available. P450$_{TYR}$ including the 35S-promoter and CaMV polyadenylation signal is excised from pRT101.79 using SphI. To generate plasmid pPZP111.79 the ends are blunt-ended with Klenow polymerase and the fragment obtained is ligated into EcoRI cut plasmid pPZP111 (Hajdukiewicz et al, Plant Mol Biol 25: 989–994, 1994), the ends of which have been blunt-ended with Klenow polymerase, too, and dephosphorylated.

For the construction of pPZP221.71E1 the cDNA clone of P450$_{OX}$ is first excised with KpnI and XbaI and ligated into the KpnI and XbaI sites of pRT101, generating pRT101.71E1. Subsequently P450$_{OX}$ including the 35S-promoter and CaMV polyadenylation signal is excised from pRT101.71E1 with HindIII and ligated into the HindIII site of pPZP221 (Hajdukiewicz et al, Plant Mol Biol 25: 989–994, 1994) thus generating pPZP221.71E1. For the construction of pPZP111.79.71E1 the cDNA clone of P450$_{OX}$ including the 35S-promoter and the CaMV polyadenylation signal is excised from pPZP221.71E1 using HindIII, blunt-ended with Klenow polymerase and ligated into the SmaI site of pPZP111.79.

9.2 Transformation of *Arabidopsis thaliana*

The binary vectors pPZP111, pPZP221, pPZP111.79, pPZP221.71E1, and pPZP111.79.71E1 are introduced into *Agrobacterium tumefaciens* strain C58C1/pGV3850 by electroporation as described by Wenjun and Forde, Nucleic Acids Research 17: 8385, 1989. *Arabidopsis thaliana* ecotype Colombia is transformed by vacuum infiltration essentially as described by the method of Bechtold et al, Molecular Biology and Genetics 316: 1194–1199, 1993. Transformants are selected on MS plates containing either 50 µg/ml kanamycin for the pPZP111 vector series, or 200 µg/ml gentamycin sulfate for the pPZP221 vector series. 4 to 6 weeks after germination kanamycin or gentamycin resistant plants are transferred to soil.

9.3 Transformation of *Nicotiana tabacum* cv Xhanti

*Nicotiana tabacum* cv Xhanti is transformed essentially by the leaf disc method of Svab et al (Methods in Plant Molecular Biology, Cold Spring Harbor, pp. 55–60, 1995) using *Agrobacterium tumefaciens* C58C1/pGV3850 transformed with either pPZP111.79, pPZP221.71E1, or pPZP111.79.71E1. 100 µg/ml kanamycin is used for selection of transformants with the pPZP111.79 vector, 100 µg/ml gentamycin sulfate for selection of transformants with the pPZP221.71E1 vector, and 50 µg/ml G-418 for selection of transformants with the pPZP111.79.71E1 vector. After rooting the tobacco plants are transferred to soil and grown in a greenhouse.

9.4 Determination of Dhurrin

The dhurrin content is quantified using the spectrophotometric cyanide assay previously described by Halkier et al (Plant Physiol 90: 1552–1559, 1989) except that 5–10 mg of leaf tissue is frozen and thawed three times before adding 0.1 mg β-d-glucosidase Type II (Sigma).

9.5 Analysis of Transgenic *Arabidopsis thaliana*

Detached leaves of *A. thaliana* are fed 2 µl of (U-14C)-tyrosine (0.05 µCi/µl, 443 mCi/mmol, Amersham), and left over night in 100 µl H$_2$O in closed eppendorf tubes. Metabolites are extracted with boiling 90% methanol for 5 min, the extracts concentrated, and applied to TLC sheets (Silica gel 60 F$_{254}$). Metabolites are separated in three different solvent systems depending on their hydrophobicity/hydrophilicity. The solvent system ethyl acetate/acetone/dichloromethane/methanol/water (20/15/6/5/4, v/v/v/v/v) preferentially separates the different cyanogenic glucosides. The solvent system isopropanol/ethyl acetate/water (7/1/2) separates the different glucosinolates. The solvent system toluene/ethyl acetate (5/1) separates the hydrophobic intermediates. Radiolabelled substrates and products are visualized using a STORM 840 phosphorimager (Molecular Dynamics, USA).

Methanol extracts of *A. thaliana* leaves analyzed by TLC of plants transformed with both P450$_{TYR}$ and P450$_{OX}$ using *A. tumefaciens* C58C1/pGV3850/pPZP111.79.71E1 reveals the presence of a new compound that co-migrates with the cyanogenic glucoside dhurrin. Feeding radiolabelled tyrosine to detached leaves shows that the radiolabel is contained in the band that co-migrates with dhurrin. Analysis of whole leaf tissue of the transformed plants by a colorimetric cyanide assay (Lambert et al., 1975, Analytic Chemistry 47, 917–919) reveals that the T1 transformants contained between 1 and 6 nmol cyanide/mg fresh weight. In comparison, control plants only transformed with nptII using *A. tumefaciens* C58C1/pGV3850/pPZP111 showed a cyanide content of 1.2±0.35 nmol cyanide/mg fresh weight. Wild-type plants of *A. thaliana* have not been reported to contain cyanogenic glucosides, and the apparent levels of cyanide detected in the control plants most likely reflects the presence of thiocyanates. Thiocyanates are breakdown products of glucosinolates, and are known to give a false reaction in the colorimetric cyanide assay (Epstein, 1974, Analytic Chemistry 19, 272–274). The observed production of large amounts of the cyanogenic glucoside dhurrin as a result of the introduction of both P450$_{TYR}$ and P450$_{OX}$ as exemplified with *A. thaliana* demonstrates that a suitable UDP-glucosyltransferase is present which glucosylates the p-hydroxymandelonitrile formed in the correct position. Since the stereospecificity of the glycosyltransferase is not known the possibility exists that the cyanogenic glucoside produced is actually taxiphyllin which is the epimer (mirror image isomer) of dhurrin.

When P450$_{TYR}$ is introduced by *A. tumefaciens* C58C1/pGV3850/pPZP111.79 into *A. thaliana* large quantities of a compound that co-migrates with the tyrosine derived glucosinolate p-hydroxybenzyl glucosinolate accumulates. This documents that the introduction of P450$_{TYR}$ results in the generation of p-hydroxyphenylacetaldoxime from tyrosine. The tyrosine derived oxime is then further metabolized by the enzymes in the glucosinolate pathway to p-hydroxybenzyl glucosinolate. This strongly indicates that the enzymes downstream of the oxime in the glucosinolate pathway have a low substrate specificity with respect to the structure of the side chain and that the glucosinolate profile in general is determined by the substrate specificity of the first cytochrome P450 in the pathway.

The substrate specificity of $P450_{OX}$ is not as narrow as that of $P450_{TYR}$. $P450_{OX}$ can metabolize other amino acid derived oximes as exemplified by the phenylalanine derived oxime, phenylacetaldoxime, whereas $P450_{TYR}$ can only metabolize tyrosine. By introducing $P450_{OX}$ into glucosinolate producing plants, it can therefore be expected that cyanogenic glucosides accumulate as generated from amino acid derived oximes in the glucosinolate biosynthetic pathway.

Because $P450_{TYR}$ and $P450_{OX}$ interact with the enzymes and the precursors in the glucosinolate biosynthetic pathway it is expected that the glucosinolate profile will also be altered.

9.6 Analysis of Transgenic *Nicotiana tabacum* cv Xhanti

Microsomes isolated from tobacco plants transformed with pPZP111.79 and functionally expressing CYP79 catalyze the formation of tyrosine to p-hydroxyphenylacetaldoxime. Methanol extracts from detached tobacco leaves expressing CYP79 and fed radioactive labeled tyrosine contain three additional labeled bands compared to wild-type tobacco plants when analyzed by TLC using the solvent system isopropanol/ethyl acetate/water (7/1/2). The additional three bands co-migrate on the TLC's with labeled bands detected in wild-type tobacco plants fed radioactive labeled p-zydroxy- phenylacetaldoxime. When analyzed in the solvent system toluene/ethyl acetate (5/1) one of the bands is confirmed to be p-hydroxyphenylacetaldoxime as evidenced by co-migration with cold standards. The identity of the two additional bands is not yet know, but from their mobility in the two solvent systems they are judged to be less hydrophobic than p-hydroxyphenylacetaldoxime, and most likely they are glycosylated derivatives of p-hydroxyphenylacetaldoxime. Analyzes of the CYP79 plants confirms that CYP79 can be expressed functionally in tobacco and that some free p-hydroxyphenylacetaldoxime is generated, but that the majority of the p-hydroxyphenylacetaldoxime generated is further metabolized by the plants. Plants expressing both $P450_{TYR}$ and $P450_{OX}$ can be obtained by crossing plant expressing $P450_{TYR}$ with plants expressing $P450_{OX}$. Alternatively, plants expressing $P450_{TYR}$ or $P450_{OX}$ can be re-transformed with *A. tumefaciens* C58C1/pGV3850/pPZP221.71E1 or *A. tumefaciens* C58C1/pGV3850/pPZP111.79 taking advantage of the fact that the two cytochromes P450 constructs are linked to the two different non exclusive resistant markers, nptII and aacCI.

Example 10
Expression of Dhurrin in Transgenic Maize
10.1 Construction of Vector Plasmids The following two vectors, pCIB 9842 and pCIB 9833, are generated for biolistic transformation of maize with $P450_{TYR}$ and $P450_{OX}$.

pCIB 9842: A cDNA clone encoding $P450_{TYR}$ cloned into the EcoRI site of pBluescript II SK as described in WO 95/16041 is used to generate a BamHI site at the start ATG codon and a Bgl II site at the stop codon by PCR. The BamHI-Bgl II fragment containing the $P450_{TYR}$ gene is cloned into BamHI and Bgl II cut pCIB 9805, a pUC19 based plant expression vector engineered with AflII/NotI/AscI sites 256 base pairs upstream from the the HindIII site and 778 bp downstream from the BgIII site and containing the metallothionin-like promoter disclosed in EP-A-452269 and the 35S terminator.

pCIB 9833: The $P450_{OX}$ cDNA clone of Example cloned into a NotI-BstXI site of pcDNAII (Invitrogen) is used to generate a BamHI site at the start ATG codon and a Bgl II site at the stop codon. The BamHI-Bgl II fragment containing the $P450_{OX}$ gene is cloned into pCIB 9805 cut with BamHI and Bgl II, too.

10.2 Methods of Transformation of Maize

Type I embryogenic callus cultures (Green et al, 1983; Wan et al, 1994) of a Lancaster-type inbred are initiated from immature embryos, 1.5–2.5 mm in length. Embryos are aseptically excised from surface-sterilized, greenhouse-grown ears approximately 14 days after pollination, placed on Duncan's callus initiation medium with 2% sucrose and 5 mg/l chloramben, and cultured in the dark. Embryogenic responses are removed from the explants after about 14 days and placed onto Duncan's maintenance medium with 2% sucrose and 0.5 mg/l 2,4-d. After 4 to 8 weeks of weekly subculture to fresh maintenance medium, high quality compact embryogenic cultures are established. Actively growing embryogenic callus pieces are selected as target tissue for gene delivery. The callus pieces are plated onto target plates containing maintenance medium with 12% sucrose approximately 4 hours prior to gene delivery. The callus pieces are arranged in circles, 8 and 10 mm from the center of the target plate. Plasmid DNA is precipitated onto gold microcarriers as described in the DuPont Biolistics manual. Two to three µg of each plasmid is used in each 6 shot microcarrier preparation. Genes are delivered to the target tissue cells using the PDS-1000He Biolistics device. The settings on the Biolistics device were as follows: 8 mm between the rupture disc and the macrocarrier, 10 mm between the macrocarrier and the stopping screen and 7 cm between the stopping screen and the target. Each target plate is shot twice using 650 psi rupture discs. A 200×200 stainless steel mesh (McMaster-Carr, New Brunswick, N.J.) is placed between the stopping screen and the target tissue. Seven days after gene delivery, target tissue pieces are transferred from the high osmotic medium to selection medium containing 100–120 mg/l glufosinate ammonium (Basta). All amino acids are removed from the selection medium. After 5 to 8 weeks on high level selection medium, any growing colonies are subcultured to medium containing 20 mg/l Basta. The embryogenic callus is subcultured every 2 weeks for 4 to 8 weeks and then transferred to a modified MS medium containing 3% sucrose, 0.25 mg/l ancymidol, 0.5 mg/l kinetin and no selection agent and placed in the light. Ancymidol and kinetin are removed after 2 weeks. Regenerating shoots with or without roots are transferred to Magenta boxes containing MS medium with 3% sucrose and small plants with roots are eventually recovered and transferred to soil in the greenhouse.

Example 11
Identification of $P450_{TYR}$ Homologues in Glucosinolate Containing Species by PCR Based on a computer sequence alignment of an Arabidopsis $P450_{TYR}$ homologue EST (accession number T42902) and a $P450_{TYR}$ homologue from Sinapis two degenerate primer oligonucleotides are designed which allow to amplify PCR fragments of $P450_{TYR}$ homologues from genomic DNA of glucosinolate containing species. Sense strand primer (5'-GCGGAATTCAARCCIGARMGIC-AYYT-3') covers the conserved amino acid sequence KPERHL (SEQ ID NO: 18) and includes an EcoRI cloning site. Antisense strand primer 2 (5'-GCGGATCCRCAICCICKYTTICCNGT-3') covers the conserved amino acid sequence TGKRGC (SEQ ID NO: 19) and includes a BamHI cloning site. PCR is performed on genomic DNA prepared with the Nucleon Phytopure Plant DNA Extraction kit of Amersham. PCR reactions are set up in a total volume of 100 µl containing 5% DMSO, 200 µM dNTPs, 200 pmol of each primer, 2.5 units Taq polymerase in PCR buffer (50 mM KCl, 10 mM Tris-HCl (pH 8.8), 1.5 mM MgCl$_2$, and 0.1% Triton X-100) using 1 µg of genomic DNA from either *Sinapis alba, A. thaliana, Brassica napus, Tropaeolum majus*, or *N. tabacum* cv Xhanti. PCR is performed using four sequential stages:

stage 1: one cycle of 5 min at 95° C.;

stage 2: 5 cycles of 30 s at 95° C., 30 s at 55° C., 30 s at 72° C.;

stage 3: 30 cycles of 30 s at 95° C., 30 s at 60° C., 30 s at 72° C.; and stage 4: one cycle of 5 min at 72° C.

To generate sufficient amounts of the approximately 100 bp band from *T. majus*, stage 2 can be modified to 5 cycles of 30 s at 95° C., 30 s at 50° C., 30 s at 71° C. PCR products are purified using the QIAquick PCR Purification Kit (Qiagen), restriction digested with EcoRI and BamHI and separated on a 3% TAE agarose gel. The dominant approximately 100 bp band is excised, and ligated into EcoRI/BamHI linearized pBluescript II SK (Stratagene). Approximately 10 clones from each of the 5 species are sequenced using the Thermo Sequence Fluorescent-labelled Primer cycle sequencing kit (7-deaza dGTP) (Amersham) and analyzed on an ALF-Express (Pharmacia).

From the four glucosinolate containing species *S. alba, A. thaliana, B. napus*, and *T. majus* PCR fragments encoding the conserved amino acid sequence, KPERH(L/F)NECSEVTLT ENDLRFISFSTGKRGC (SEQ ID NOs: 20 and 21, respectively) are identified. This consensus amino acid sequence is identical to the P450$_{TYR}$ homologue sequences from *S. alba* and *A. thaliana* previously identified and highly similar to the sorghum P450$_{TYR}$ amino acid sequence. From the non-glucosinolate containing plant *N. tabacum* cv Xhanti a PCR fragment encoding this consensus sequence could not be identified. The presence of this P450$_{TYR}$ homologue consensus amino acid sequence in the exemplified four glucosinolate containing plant species indicates that an amino acid N-hydroxylase cytochrome P450 of the P450$_{TYR}$ family converts the parent amino acids or chain elongated parent amino acids into the corresponding oximes in glucosinolate species. The generation of PCR fragments specific for the P450$_{TYR}$ homologues allow the isolation of homologous cDNA or genomic clones from corresponding libraries.

Although the foregoing invention has been described in some detail by way of illustration and example for purposes of clarity of understanding, it will be obvious that certain changes and modifications may be practiced within the scope of the appended claims.

What is claimed is:

1. A cytochrome P450 monooxygenase that catalyzes the conversion of an aldoxime to the corresponding nitrile and the conversion of said nitrile to the corresponding cyanohydrin, wherein said cytochrome P450 monooxygenase comprises an amino acid sequence encoded by a nucleotide sequence, the complement of which hybridizes to SEQ ID NO: 1 under hybridization conditions comprising:

hybridization in 5×SSC, 0.1% N-lauroylsarcosine, 0.02% SDS at 68° C., and washing twice for 15 minutes in 0.1×SSC, 0.1% SDS at 65° C.

2. The cytochrome P450 monooxygenase according to claim 1, wherein said cytochrome P450 monooxygenase has a molecular weight of 55 kD, as determined by SDS-PAGE.

3. The cytochrome P450 monooxygenase according to claim 1, wherein said cytochrome P450 monooxygenase comprises the amino acid sequence shown in SEQ ID NO:2.

4. The cytochrome P450 monooxygenase according to claim 1, wherein said cytochrome P450 monooxygenase comprises an N-terminal sequence as shown in SEQ ID NO:3.

5. The cytochrome P450 monooxygenase according to claim 1, wherein said cytochrome P450 monooxygenase comprises an internal sequence as shown in SEQ ID NO:4.

6. The cytochrome P450 monooxygenase according to claim 1, wherein said cytochrome P450 monooxygenase is isolated from a plant that produces cyanogenic glycosides.

7. The cytochrome P450 monooxygenase according to claim 1, wherein said cytochrome P450 monooxygenase is isolated from Sorghum.

8. The cytochrome P450 monooxygenase according to claim 1, wherein said cytochrome P450 monooxygenase is isolated from Sorghum bicolor.

9. The cytochrome P450 monooxygenase according to claim 1, wherein the aldoxime is obtained by the conversion of an amino acid selected from the group consisting of tyrosine, phenylalanine, tryptophan, valine, leucine, isoleucine and cyclopentenylglycine in the presence of another cytochrome P-450 monooxygenase that catalyzes the conversion of said amino acid to the corresponding N-hydroxyamino acid and the conversion of said N-hydroxy-amino acid to said aldoxime.

* * * * *